US012077563B2

(12) United States Patent
McLellan et al.

(10) Patent No.: US 12,077,563 B2
(45) Date of Patent: *Sep. 3, 2024

(54) PREFUSION-STABILIZED HMPV F PROTEINS

(71) Applicant: BOARD OF REGENTS, THE UNIVERSITY OF TEXAS SYSTEM, Austin, TX (US)

(72) Inventors: Jason McLellan, Austin, TX (US); Ching-Lin Hsieh, Austin, TX (US); Scott Rush, Austin, TX (US); Nianshuang Wang, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/411,284

(22) Filed: Jan. 12, 2024

(65) Prior Publication Data

US 2024/0140994 A1    May 2, 2024

Related U.S. Application Data

(63) Continuation of application No. 18/296,771, filed on Apr. 6, 2023, now Pat. No. 11,919,927, which is a continuation of application No. PCT/US2021/053944, filed on Oct. 7, 2021.

(60) Provisional application No. 63/089,978, filed on Oct. 9, 2020.

(51) Int. Cl.
  *C07K 14/08*  (2006.01)
  *C07K 14/115*  (2006.01)
  *C07K 14/135*  (2006.01)

(52) U.S. Cl.
  CPC .................... *C07K 14/08* (2013.01)

(58) Field of Classification Search
  None
  See application file for complete search history.

(56) References Cited

U.S. PATENT DOCUMENTS

| | | | |
|---|---|---|---|
| 9,738,689 B2 | 8/2017 | Kwong et al. | |
| 10,017,543 B2 | 7/2018 | Kwong et al. | |
| 2018/0008697 A1 | 1/2018 | Kwong et al. | |
| 2021/0206806 A1 | 7/2021 | Larraillet et al. | |
| 2023/0174587 A1* | 6/2023 | Kwong ................ | A61K 39/155 424/186.1 |

FOREIGN PATENT DOCUMENTS

| WO | WO 2014/160463 | 10/2014 |
|---|---|---|
| WO | WO 2016/103238 | 6/2016 |
| WO | WO 2020/234300 | 11/2020 |
| WO | WO 2021/222639 | 11/2021 |
| WO | WO 2023/110618 | 6/2023 |

OTHER PUBLICATIONS

Adams et al. "PHENIX: building new software for automated crystallographic structure determination." Acta crystallographica. Section D, Biological crystallography 58, 1948-1954 (2002).
Baden et al. Efficacy and Safety of the mRNA-1273 SARS-COV-2 Vaccine. The New England journal of medicine (2020) doi:10.1056/NEJMoa2035389.
Bangaru et al. A Site of Vulnerability on the Influenza Virus Hemagglutinin Head Domain Trimer Interface. Cell 177, 1136-1152.e18 (2019).
Battles et al. Structure and immunogenicity of pre-fusion-stabilized human metapneumovirus F glycoprotein. Nature communications 8, 1528 (2017).
Battye et al. iMOSFLM: a new graphical interface for diffraction-image processing with MOSFLM. Acta crystallographica. Section D, Biological crystallography 67, 271-281 (2011).
Benjamini et al. Adaptive linear step-up procedures that control the false discovery rate. Biometrika 93, 491-507 (2006).
Chang, Andres, et al. "Potential electrostatic interactions in multiple regions affect human metapneumovirus F-mediated membrane fusion." *Journal of Virology* 86.18 (2012): 9843-9853.
Corti et al. Cross-neutralization of four paramyxoviruses by a human monoclonal antibody. Nature 501, 439-443 (2013).
Crank et al. A proof of concept for structure-based vaccine design targeting RSV in humans. Science 365, 505-509 (2019).
Deffrasnes, Celine, Marie-Eve Hamelin, and Guy Boivin. "Human metapneumovirus." *Seminars in respiratory and critical care medicine*. Vol. 28. No. 02. Copyright© 2007 by Thieme Medical Publishers, Inc., 333 Seventh Avenue, New York, NY 10001, USA., 2007.
Dubois et al. "Mutations in the fusion protein heptad repeat domains of human metapneumovirus impact on the formation of syncytia." *The Journal of general virology* vol. 98,6 (2017): 1174-1180.
Emsley & Cowtan, Coot: Model-building tools for molecular graphics. Acta Crystallographica Section D: Biological Crystallography 60, 2126-2132 (2004).
Evans & Murshudov, How good are my data and what is the resolution? Acta crystallographica. Section D, Biological crystallography 69, 1204-1214 (2013).
GenBank Accession No. AAK62968.2, "fusion protein [Human metapneumovirus]," Apr. 15, 2002.
GenBank Accession No. AAS92882.1, "fusion protein [Human metapneumovirus]," Jan. 22, 2008.
GenBank Accession No. ACJ70115.1, "fusion protein [Human metapneumovirus]," Dec. 9, 2008.
GenBank Accession No. AY525843.1, "Human metapneumovirus isolate NL/1/99, complete genome," Jan. 22, 2008.
Gilman et al. Rapid profiling of RSV antibody repertoires from the memory B cells of naturally infected adult donors. Science Immunology 1, eaaj1879 (2016).
Gilman et al. Transient opening of trimeric prefusion RSV F proteins. Nature Communications 10, 2105 (2019).
Graham, Vaccine development for respiratory syncytial virus. Current opinion in virology 23, 107-112 (2017).

(Continued)

*Primary Examiner* — Nianxiang Zou
(74) *Attorney, Agent, or Firm* — Parker Highlander PLLC

(57) ABSTRACT

Provided herein are engineered hMPV F proteins. In some aspects, the engineered F proteins exhibit enhanced conformational stability and/or antigenicity. Methods are also provided for use of the engineered F proteins as diagnostics, in screening platforms, and/or in vaccine compositions.

28 Claims, 11 Drawing Sheets

Specification includes a Sequence Listing.

(56) References Cited

OTHER PUBLICATIONS

Grant et al. cisTEM, user-friendly software for single-particle image processing. eLife 7, (2018).
Hsieh et al. Structure-based design of prefusion-stabilized SARS-COV-2 spikes. Science 369, 1501 LP-1505 (2020).
Huang et al. Antibody recognition of the Pneumovirus fusion protein trimer interface. PLoS pathogens 16, e1008942 (2020).
Huang et al. Structure, Immunogenicity, and Conformation-Dependent Receptor Binding of the Postfusion Human Metapneumovirus F Protein. Journal of Virology 95, e00593-21 (2021).
International Preliminary Report on Patentability issued in International Application No. PCT/US2021/053944, dated Apr. 20, 2023.
International Search Report and Written Opinion issued in International Application No. PCT/US2021/053944, dated Mar. 7, 2022.
Joyce et al. Iterative structure-based improvement of a fusion-glycoprotein vaccine against RSV. Nature structural & molecular biology 23, 811-820 (2016).
Keech et al. Phase 1-2 Trial of a SARS-COV-2 Recombinant Spike Protein Nanoparticle Vaccine. The New England journal of medicine 383, 2320-2332 (2020).
Krarup et al. A highly stable prefusion RSV F vaccine derived from structural analysis of the fusion mechanism. Nature communications 6, 8143 (2015).
Magro et al. Neutralizing antibodies against the preactive form of respiratory syncytial virus fusion protein offer unique possibilities for clinical intervention. Proceedings of the National Academy of Sciences of the United States of America 109, 3089-3094 (2012).
Más et al. Engineering, Structure and Immunogenicity of the Human Metapneumovirus F Protein in the Postfusion Conformation. PLoS pathogens 12, e1005859 (2016).
McCoy et al. Phaser crystallographic software. Journal of applied crystallography 40, 658-674 (2007).
McLellan et al. Structure-based design of a fusion glycoprotein vaccine for respiratory syncytial virus. Science (New York, N.Y.) 342, 592-598 (2013).
Punjani et al. cryoSPARC: algorithms for rapid unsupervised cryo-EM structure determination. Nature methods 14, 290-296 (2017).
Rutten et al. A Universal Approach to Optimize the Folding and Stability of Prefusion-Closed HIV-1 Envelope Trimers. Cell reports 23, 584-595 (2018).
Rutten et al. Structure-Based Design of Prefusion-Stabilized Filovirus Glycoprotein Trimers. Cell reports 30, 4540-4550.e3 (2020).
Sanders et al. A next-generation cleaved, soluble HIV-1 Env trimer, BG505 SOSIP.664 gp140, expresses multiple epitopes for broadly neutralizing but not non-neutralizing antibodies. PLoS pathogens 9, e1003618 (2013).
Sastre et al. Comparison of affinity chromatography and adsorption to vaccinia virus recombinant infected cells for depletion of antibodies directed against respiratory syncytial virus glycoproteins present in a human immunoglobulin preparation. Journal of medical virology 76, 248-255 (2005).
Schickli et al., An S101P substitution in the putative cleavage motif of the human metapneumovirus fusion protein is a major determinant for trypsin-independent growth in vero cells and does not alter tissue tropism in hamsters. Journal of virology 79, 10678-10689 (2005).
Shafagati & Williams, Human metapneumovirus—what we know now [ version 1 ; referees : 2 approved ] Referee Status : F1000 Research 7, 1-11 (2018).
Shirogane et al. Efficient Multiplication of Human Metapneumovirus in Vero Cells Expressing the Transmembrane Serine Protease TMPRSS2. Journal of Virology 82, 8942-8946 (2008).
Skiadopoulos et al. Individual contributions of the human metapneumovirus F, G, and SH surface glycoproteins to the induction of neutralizing antibodies and protective immunity. Virology 345, 492-501 (2006).
Stewart-Jones et al. Structure-based design of a quadrivalent fusion glycoprotein vaccine for human parainfluenza virus types 1-4. Proceedings of the National Academy of Sciences of the United States of America 115, 12265-12270 (2018).
Van den Hoogen et al. A newly discovered human pneumovirus isolated from young children with respiratory tract disease. Nature medicine 7, 719-724 (2001).
Van den Hoogen et al. Analysis of the genomic sequence of a human metapneumovirus. Virology 295, 119-132 (2002).
Watanabe et al. Antibodies to a Conserved Influenza Head Interface Epitope Protect by an IgG Subtype-Dependent Mechanism. Cell 177, 1124-1135.e16 (2019).
Wen et al. Structural basis for antibody cross-neutralization of respiratory syncytial virus and human metapneumovirus. Nature microbiology 2, 16272 (2017).
Wen et al. Structure of the human metapneumovirus fusion protein with neutralizing antibody identifies a pneumovirus antigenic site. Nature structural & molecular biology 19, 461-463 (2012).
Williams et al. Phase 1 Safety and Immunogenicity Study of a Respiratory Syncytial Virus Vaccine With an Adenovirus 26 Vector Encoding Prefusion F (Ad26.RSV.preF) in Adults Aged ≥60 Years. The Journal of infectious diseases 222, 979-988 (2020).
Wrapp et al. Cryo-EM structure of the 2019-nCOV spike in the prefusion conformation. Science 367, 1260 LP-1263 (2020).

* cited by examiner

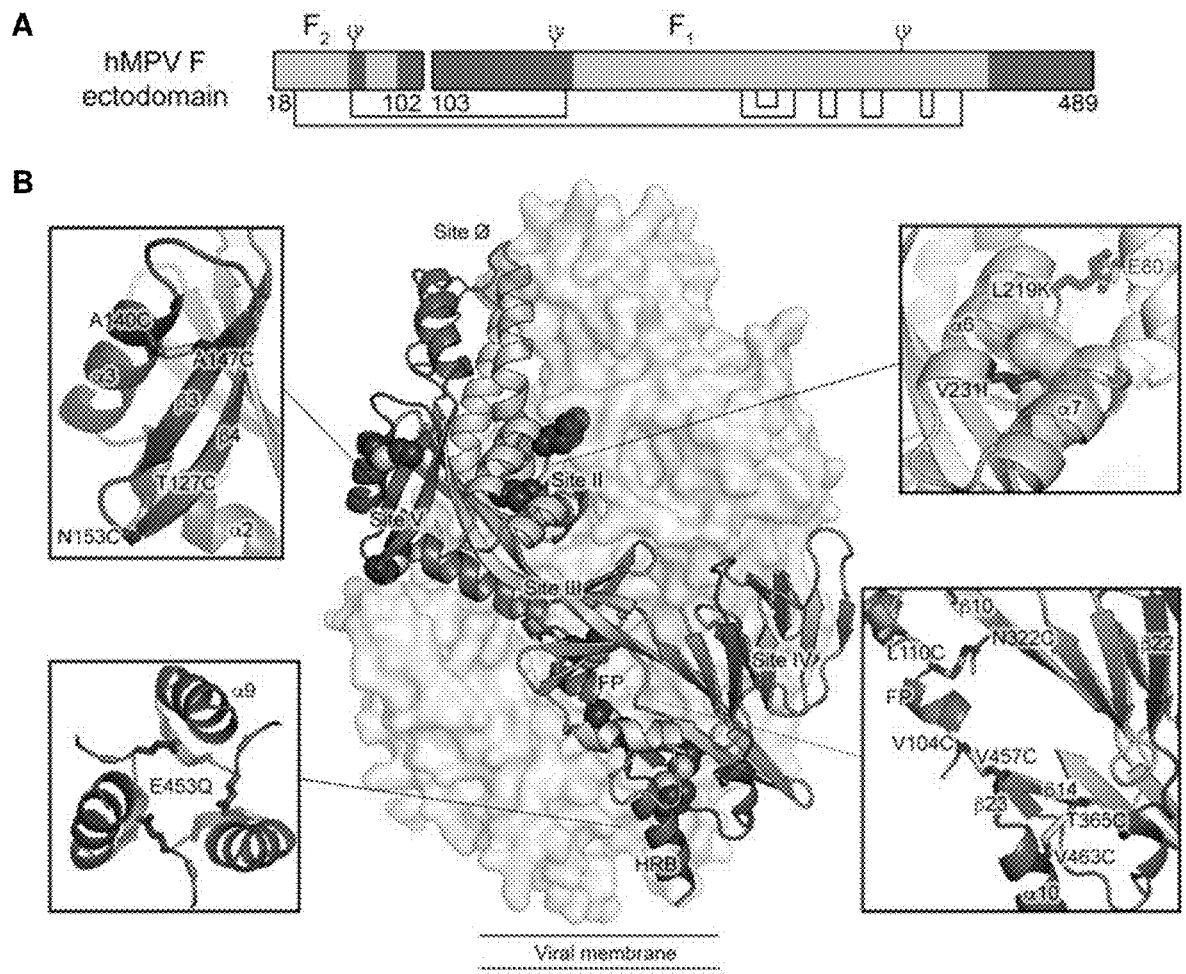
FIGS. 1A-B

Cavity mutations

Disulfide mutations

Proline mutations

Electrostatic mutations

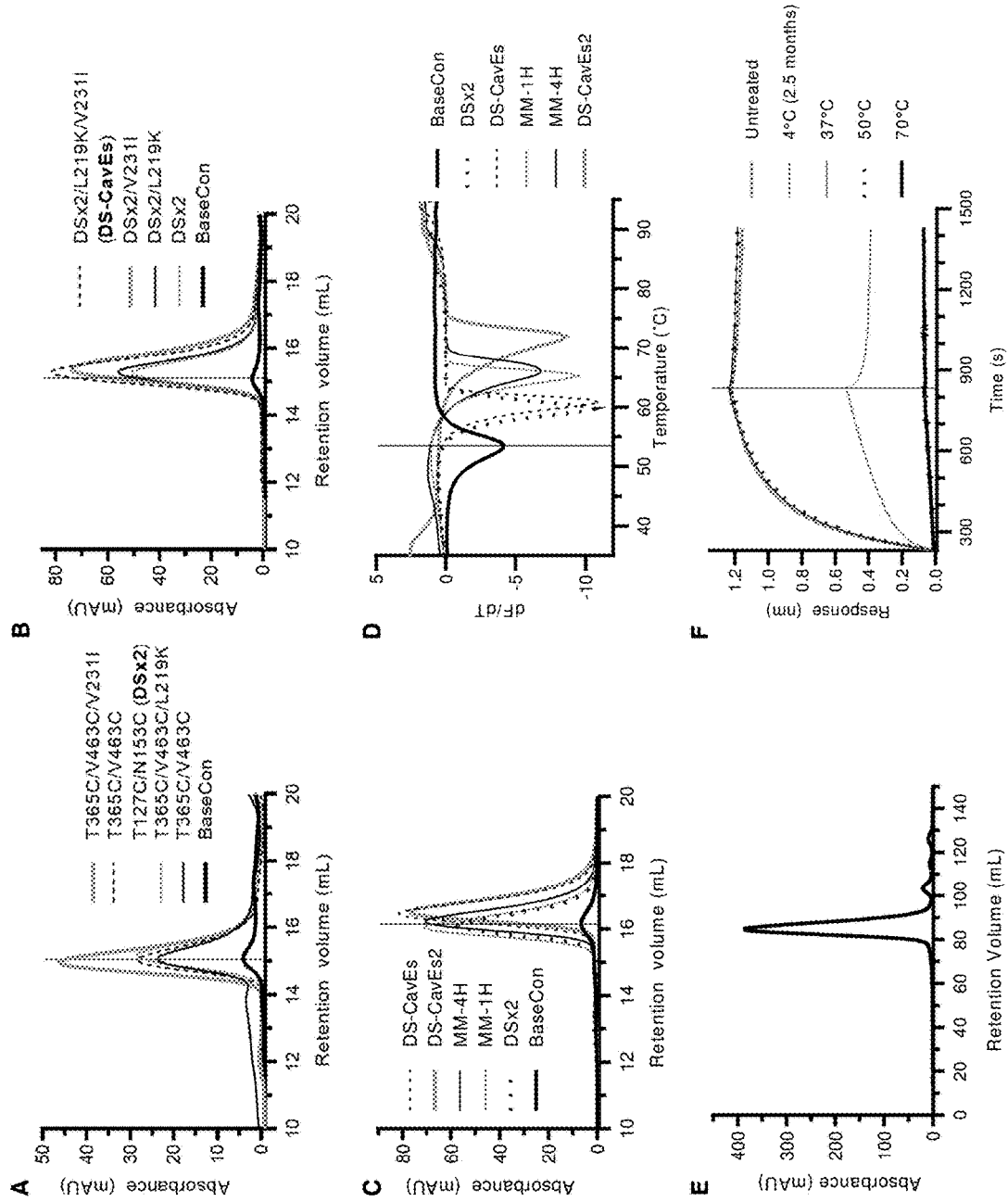
FIGS. 4A-F

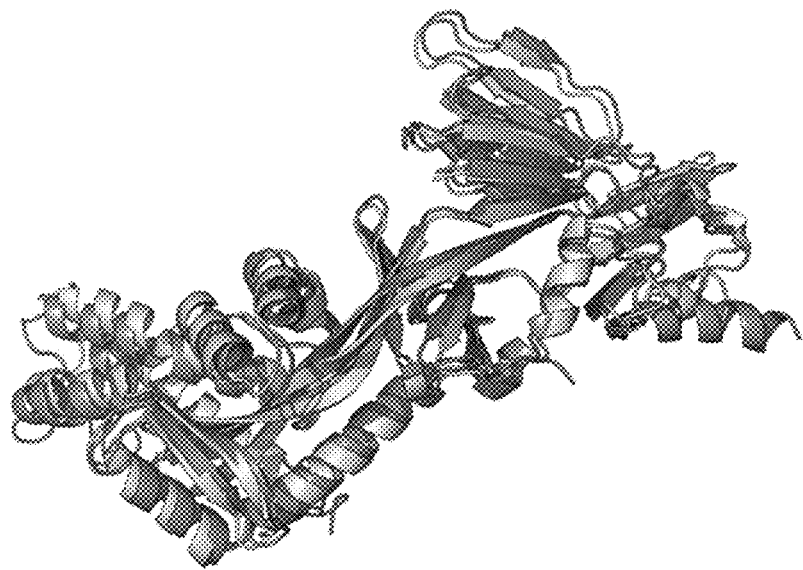
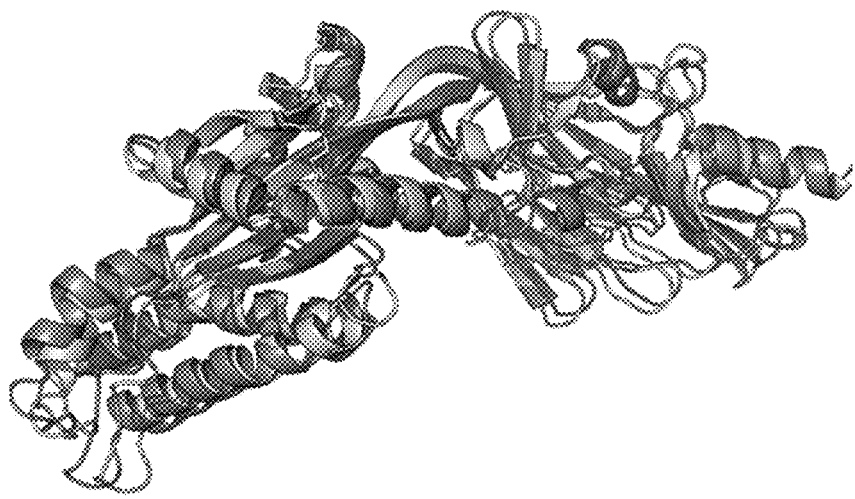
FIG. 9

SEQUENCE LISTING

```
Sequence total quantity: 17
SEQ ID NO: 1            moltype = AA  length = 559
FEATURE                 Location/Qualifiers
source                  1..559
                        mol_type = protein
                        organism = synthetic construct
SEQUENCE: 1
MSWKVVIIFS LLITPQHGLK ESYLEESCST ITEGYLSVLR TGWYTNVFTL EVGDVENLTC   60
ADGPSLIKTE LDLTKSALRE LRTVSADQLA REEQIENPRR RRFVLGAIAL GVATAAAVTA  120
GVAIAKTIRL ESEVTAIKNA LKKTNEAVST LGNGVRVLAT AVRELKDFVS KNLTRAINKN  180
KCDIPDLKMA VSFSQFNRRF LNVVRQFSDN AGITPAISLD LMTDAELARA VSNMPTSAGQ  240
IKLMLENRAM VRRKGFGILI GVYGSSVIYM VQLPIFGVID TPCWIVKAAP SCSEKKGNYA  300
CLLREDQGWY CQNAGSTVYY PNEKDCETRG DHVFCDTAAG INVAEQSKEC NINISTTNYP  360
CKVSTGRHPI SMVALSPLGA LVACYKGVSC SIGSNRVGII KQLNKGCSYI TNQDADTVTI  420
DNTVYQLSKV EGEQHVIKGR PVSSSFDPVK FPEDQFNVAL DQVFESIENS QALVDQSNRI  480
```

-continued

```
LSSAEKGNTS GRENLYFQGG GSGYIPEAPR DGQAYVRKDG EWVLLSTFLG RSLEVLFQGP  540
GHHHHHHHHS AWSHPQFEK                                              559

SEQ ID NO: 2          moltype = AA  length = 551
FEATURE               Location/Qualifiers
source                1..551
                      mol_type = protein
                      organism = synthetic construct
SEQUENCE: 2
MSWKVVIIFS LLITPQHGLK ESYLEESCST ITEGYLSVLR TGWYTNVFTL EVGDVENLTC  60
ADGPSLIKTE LDLTKSALRE LRTVSADQLA REEQIENPRR RRFVLGAIAL GVATAAAVTA  120
GVAIAKTIRL ESEVTAIKNA LKKTNEAVST LGNGVRVLAT AVRELKDFVS KNLTRAINKN  180
KCDIPDLKMA VSFSQFNRRF LNVVRQFSDN AGITPAISLD LMTDAELARA VSNMPTSAGQ  240
IKLMLENRAM VRRKGFGILI GVYGSSVIYM VQLPIFGVID TPCWIVKAAP SCSEKKGNYA  300
CLLREDQGWY CQNAGSTVYY PNEKDCETRG DHVFCDTAAG INVAEQSKEC NINISTTNYP  360
CKVSTGRNPI SMVALSPLGA LVACYKGVSC SIGSNRVGII KQLNKGCSYI TNQDADTVTI  420
DNTVYQLSKV EGEQHVIKGR PVSSSFDPVK FPEDQFNVAL DQVFESIENS QALVDQSNRI  480
LSSAEKGNTG GGGSGYIPEA PRDGQAYVRK DGEWVLLSTF LGRSLEVLFQ GPGHHHHHHH  540
HSAWSHPQFE K                                                      551

SEQ ID NO: 3          moltype = AA  length = 542
FEATURE               Location/Qualifiers
source                1..542
                      mol_type = protein
                      organism = synthetic construct
SEQUENCE: 3
MSWKVVIIFS LLITPQHGLK ESYLEESCST ITEGYLSVLR TGWYTNVFTL EVGDVENLTC  60
ADGPSLIKTE LDLTKSALRE LRTVSADQLA REEQIENPRR RRFVLGAIAL GVATAAAVTA  120
GVAIAKTIRL ESEVTAIKNA LKKTNEAVST LGNGVRVLAT AVRELKDFVS KNLTRAINKN  180
KCDIPDLKMA VSFSQFNRRF LNVVRQFSDN AGITPAISLD LMTDAELARA VSNMPTSAGQ  240
IKLMLENRAM VRRKGFGILI GVYGSSVIYM VQLPIFGVID TPCWIVKAAP SCSEKKGNYA  300
CLLREDQGWY CQNAGSTVYY PNEKDCETRG DHVFCDTAAG INVAEQSKEC NINISTTNYP  360
CKVSTGRHPI SMVALSPLGA LVACYKGVSC SIGSNRVGII KQLNKGCSYI TNQDADTVTI  420
DNTVYQLSKV EGEQHVIKGR PVSSSFDPVK FPEDQFNVAL DQVFESIENS QALVDQSNRI  480
LSSAGGYIPE APRDGQAYVR KDGEWVLLST FLGRSLEVLF QGPGHHHHHH HHSAWSHPQF  540
EK                                                                542

SEQ ID NO: 4          moltype = AA  length = 539
FEATURE               Location/Qualifiers
source                1..539
                      mol_type = protein
                      organism = Human metapneumovirus
SEQUENCE: 4
MSWKVVIIFS LLITPQHGLK ESYLEESCST ITEGYLSVLR TGWYTNVFTL EVGDVENLTC  60
ADGPSLIKTE LDLTKSALRE LRTVSADQLA REEQIENPRQ SRFVLGAIAL GVATAAAVTA  120
GVAIAKTIRL ESEVTAIKNA LKKTNEAVST LGNGVRVLAT AVRELKDFVS KNLTRAINKN  180
KCDIADLKMA VSFSQFNRRF LNVVRQFSDN AGITPAISLD LMTDAELARA VSNMPTSAGQ  240
IKLMLENRAM VRRKGFGFLI GVYGSSVIYM VQLPIFGVID TPCWIVKAAP SCSGKKGNYA  300
CLLREDQGWY CQNAGSTVYY PNEKDCETRG DHVFCDTAAG INVAEQSKEC NINISTTNYP  360
CKVSTGRHPI SMVALSPLGA LVACYKGVSC SIGSNRVGII KQLNKGCSYI TNQDADTVTI  420
DNTVYQLSKV EGEQHVIKGR PVSSSFDPVK FPEDQFNVAL DQVFESIENS QALVDQSNRI  480
LSSAEKGNTG FIIVIILIAV LGSTMILVSV FIIIKKTKKP TGAPPELSGV TNNGFIPHN   539

SEQ ID NO: 5          moltype = AA  length = 539
FEATURE               Location/Qualifiers
source                1..539
                      mol_type = protein
                      organism = Human metapneumovirus
SEQUENCE: 5
MSWKVVIIFS LLITPQHGLK ESYLEESCST ITEGYLSVLR TGWYTNVFTL EVGDVENLTC  60
SDGPSLIKTE LDLTKSALRE LKTVSADQLA REEQIENPRQ SRFVLGAIAL GVATAAAVTA  120
GVAIAKTIRL ESEVTAIKNA LKTTNEAVST LGNGVRVLAT AVRELKDFVS KNLTRAINKN  180
KCDIDDLKMA VSFSQFNRRF LNVVRQFSDN AGITPAISLD LMTDAELARA VSNMPTSAGQ  240
IKLMLENRAM VRRKGFGILI GVYGSSVIYT VQLPIFGVID TPCWIVKAAP SCSEKKGNYA  300
CLLREDQGWY CQNAGSTVYY PNEKDCETRG DHVFCDTAAG INVAEQSKEC NINISTTNYP  360
CKVSTGRHPI SMVALSPLGA LVACYKGVSC SIGSNRVGII KQLNKGCSYI TNQDADTVTI  420
DNTVYQLSKV EGEQHVIKGR PVSSSFDPIK FPEDQFNVAL DQVFENIENS QALVDQSNRI  480
LSSAEKGNTG FIIVIILIAV LGSSMILVSI FIIIKKTKKP TGAPPELSGV TNNGFIPHS   539

SEQ ID NO: 6          moltype = AA  length = 539
FEATURE               Location/Qualifiers
source                1..539
                      mol_type = protein
                      organism = Human metapneumovirus
SEQUENCE: 6
MSWKVMIIIS LLITPQHGLK ESYLEESCST ITEGYLSVLR TGWYTNVFTL EVGDVENLTC  60
TDGPSLIKTE LDLTKSALRE LKTVSADQLA REEQIENPRQ SRFVLGAIAL GVATAAAVTA  120
GIAIAKTIRL ESEVNAIKGA LKQTNEAVST LGNGVRVLAT AVRELKEFVS KNLTSAINRN  180
KCDIADLKMA VSFSQFNRRF LNVVRQFSDN AGITPAISLD LMTDAELARA VSYMPTSAGQ  240
```

```
IKLMLENRAM VRRKGFGILI GVYGSSVIYM VQLPIFGVID TPCWIIKAAP SCSEKNGNYA    300
CLLREDQGWY CKNAGSTVYY PNEKDCETRG DHVFCDTAAG INVAEQSREC NINISTTNYP    360
CKVSTGRHPI SMVALSPLGA LVACYKGVSC SIGSNWVGII KQLPKGCSYI TNQDADTVTI    420
DNTVYQLSKV EGEQHVIKGR PVSSSFDPIK FPEDQFNVAL DQVFESIENS QALVDQSNKI    480
LNSAEKGNTG FIIVVILVAV LGLTMISVSI IIIIKKTRKP TGAPPELNGV TNGGFIPHS     539

SEQ ID NO: 7              moltype = AA   length = 539
FEATURE                   Location/Qualifiers
source                    1..539
                          mol_type = protein
                          organism = Human metapneumovirus
SEQUENCE: 7
MSWKVMIIIS LLITPQHGLK ESYLEESCST ITEGYLSVLR TGWYTNVFTL EVGDVENLTC    60
TDGPSLIKTE LDLTKSALRE LKTVSADQLA REEQIENPRQ SRFVLGAIAL GVATAAAVTA    120
GIAIAKTIRL ESEVNAIKGA LKTTNEAVST LGNGVRVLAT AVRELKEFVS KNLTSAINKN    180
KCDIADLKMA VSFSQFNRRF LNVVRQFSDN AGITPAISLD LMTDAELARA VSYMPTSAGQ    240
IKLMLENRAM VRRKGFGILI GVYGSSVIYM VQLPIFGVID TPCWIIKAAP SCSEKDGNYA    300
CLLREDQGWY CKNAGSTVYY PNDKDCETRG DHVFCDTAAG INVAEQSREC NINISTTNYP    360
CKVSTGRHPI SMVALSPLGA LVACYKGVSC SIGSNRVGII KQLPKGCSYI TNQDADTVTI    420
DNTVYQLSKV EGEQHVIKGR PVSSSFDPIK FPEDQFNVAL DQVFESIENS QALVDQSNKI    480
LNSAEKGNTG FIIVIILIAV LGLTMISVSI IIIIKKTRKP TGAPPELNGV TNGGFIPHS     539

SEQ ID NO: 8              moltype = AA   length = 11
FEATURE                   Location/Qualifiers
source                    1..11
                          mol_type = protein
                          organism = synthetic construct
SEQUENCE: 8
GGGGSGGGGS R                                                        11

SEQ ID NO: 9              moltype = AA   length = 4
FEATURE                   Location/Qualifiers
source                    1..4
                          mol_type = protein
                          organism = synthetic construct
SEQUENCE: 9
RQSR                                                                4

SEQ ID NO: 10             moltype = AA   length = 4
FEATURE                   Location/Qualifiers
source                    1..4
                          mol_type = protein
                          organism = synthetic construct
SEQUENCE: 10
RRRR                                                                4

SEQ ID NO: 11             moltype = AA   length = 18
FEATURE                   Location/Qualifiers
source                    1..18
                          mol_type = protein
                          organism = synthetic construct
SEQUENCE: 11
MSWKVMIIIS LLITPQHG                                                 18

SEQ ID NO: 12             moltype = AA   length = 6
FEATURE                   Location/Qualifiers
source                    1..6
                          mol_type = protein
                          organism = synthetic construct
SEQUENCE: 12
GGSGGS                                                              6

SEQ ID NO: 13             moltype = AA   length = 6
FEATURE                   Location/Qualifiers
source                    1..6
                          mol_type = protein
                          organism = synthetic construct
SEQUENCE: 13
GGGGGG                                                              6

SEQ ID NO: 14             moltype = AA   length = 454
FEATURE                   Location/Qualifiers
source                    1..454
                          mol_type = protein
                          organism = synthetic construct
SEQUENCE: 14
LKESYLEESC STITEGYLSV LRTGWYTNVF TLEVGDVENL TCADGPSLIK TELDLTKSAL    60
RELRTVSADQ LAREEQIENP RRRRFVLGAI ALGVATAAAV TAGVAIAKCI RLESEVTAIK    120
NALKKTNEAV STLGCGVRVL ATAVRELKDF VSKNLTRAIN KNKCDIPDLK MAVSFSQFNR    180
```

```
RFLNVVRQFS DNAGITPAIS KDLMTDAELA RAISNMPTSA GQIKLMLENR AMVRRKGFGI    240
LIGVYGSSVI YMVQLPIFGV IDTPCWIVKA APSCSEKKGN YACLLREDQG WYCQNAGSTV    300
YYPNEKDCET RGDHVFCDTA AGINVAEQSK ECNINISTTN YPCKVSCGRN PISMVALSPL    360
GALVACYKGV SCSIGSNRVG IIKQLNKGCS YITNQDADTV TIDNTVYQLS KVEGEQHVIK    420
GRPVSSSFDP VKFPEDQFNV ALDQCFESIE NSQA                                454

SEQ ID NO: 15          moltype = AA  length = 454
FEATURE                Location/Qualifiers
source                 1..454
                       mol_type = protein
                       organism = synthetic construct
SEQUENCE: 15
LKESYLEESC STITEGYLSV LRTGWYTNVF TLEVGDVENL TCADGPSLIK TELDLTKSAL    60
RELRTVSADQ LAREEQIENP RRRRFVLGAI ACGVATAAAV TAGVAIAKCI RLESEVTAIK    120
NCLKKTNECV STLGCGVRVL ATAVRELKDF VSKNLTRAIN KNKCDIPDLK MAVSFSQFNR    180
RFLNVVRQFS DNAGITPAIS KDLMTDAELA RAISNMPTSA GQIKLMLENR AMVRRKGFGI    240
LIGVYGSSVI YMVQLPIFGV IDTPCWIVKA APSCSEKKGN YACLLREDQG WYCQNAGSTV    300
YYPCEKDCET RGDHVFCDTA AGINVAEQSK ECNINISTTN YPCKVSCGRH PISMVALSPL    360
GALVACYKGV SCSIGSNRVG IIKQLNKGCS YITNQDADTV TIDNTVYQLS KVEGEQHVIK    420
GRPVSSSFDP VKFPQDQFNV ALDQCFESIE NSQA                                454

SEQ ID NO: 16          moltype = AA  length = 454
FEATURE                Location/Qualifiers
source                 1..454
                       mol_type = protein
                       organism = synthetic construct
VARIANT                79..84
                       note = Xaa is Gly or Ser
SEQUENCE: 16
LKESYLEESC STITEGYLSV LRTGWYTNVF TLEVGDVENL TCADGPSLIK TELDLTKSAL    60
RELRTVSADQ LAREEQIEXX XXXXFVLGAI ALGVATAAAV TAGVAIAKCI RLESEVTAIK    120
NALKKTNEAV STLGCGVRVL ATAVRELKDF VSKNLTRAIN KNKCDIPDLK MAVSFSQFNR    180
RFLNVVRQFS DNAGITPAIS KDLMTDAELA RAISNMPTSA GQIKLMLENR AMVRRKGFGI    240
LIGVYGSSVI YMVQLPIFGV IDTPCWIVKA APSCSEKKGN YACLLREDQG WYCQNAGSTV    300
YYPNEKDCET RGDHVFCDTA AGINVAEQSK ECNINISTTN YPCKVSCGRN PISMVALSPL    360
GALVACYKGV SCSIGSNRVG IIKQLNKGCS YITNQDADTV TIDNTVYQLS KVEGEQHVIK    420
GRPVSSSFDP VKFPEDQFNV ALDQCFESIE NSQA                                454

SEQ ID NO: 17          moltype = AA  length = 454
FEATURE                Location/Qualifiers
source                 1..454
                       mol_type = protein
                       organism = synthetic construct
VARIANT                79..84
                       note = Xaa is Gly or Ser
SEQUENCE: 17
LKESYLEESC STITEGYLSV LRTGWYTNVF TLEVGDVENL TCADGPSLIK TELDLTKSAL    60
RELRTVSADQ LAREEQIEXX XXXXFVLGAI ACGVATAAAV TAGVAIAKCI RLESEVTAIK    120
NCLKKTNECV STLGCGVRVL ATAVRELKDF VSKNLTRAIN KNKCDIPDLK MAVSFSQFNR    180
RFLNVVRQFS DNAGITPAIS KDLMTDAELA RAISNMPTSA GQIKLMLENR AMVRRKGFGI    240
LIGVYGSSVI YMVQLPIFGV IDTPCWIVKA APSCSEKKGN YACLLREDQG WYCQNAGSTV    300
YYPCEKDCET RGDHVFCDTA AGINVAEQSK ECNINISTTN YPCKVSCGRH PISMVALSPL    360
GALVACYKGV SCSIGSNRVG IIKQLNKGCS YITNQDADTV TIDNTVYQLS KVEGEQHVIK    420
GRPVSSSFDP VKFPQDQFNV ALDQCFESIE NSQA                                454
```

PREFUSION-STABILIZED HMPV F PROTEINS

REFERENCE TO RELATED APPLICATIONS

The present application is a continuation of U.S. application Ser. No. 18/296,771, filed Apr. 6, 2023, which is a continuation of International Application No. PCT/US2021/053944, filed Oct. 7, 2021, which claims the priority benefit of U.S. provisional application No. 63/089,978, filed Oct. 9, 2020, the entire contents of each of which is incorporated herein by reference.

REFERENCE TO A SEQUENCE LISTING

The instant application contains a Sequence Listing XML, which has been submitted electronically and is hereby incorporated by reference in its entirety. Said Sequence Listing XML, created on Jan. 12, 2024, is named UTSBP1250USC1.xml and is 22,063 bytes in size.

BACKGROUND

1. Field

The present disclosure relates generally to the fields of medicine, virology, immunology, and protein engineering. More particular, the disclosure relates to engineered human metapneumovirus (hMPV) F proteins and the use thereof in drug design and vaccine formulation.

2. Description of Related Art

Human metapneumovirus (hMPV) is a respiratory virus of the Pneumoviridae family that has been circulating in humans for at least a half century prior to its discovery in 2001 (van den Hoogen et al., 2001). There is near ubiquitous infection by the age of five and re-infections continue to be a burden throughout life (van den Hoogen et al., 2001). However, infants (6-12 months), the elderly, and immunocompromised populations are at an increased risk of hospitalization with more severe disease such as pneumonia and bronchiolitis (Deffrasnes et al., 2007). Despite the disease burden that hMPV presents, there are no vaccines or therapeutics that have been approved for prevention or treatment. As a member of the Pneumoviridae family recently elevated from a subfamily within Paramyxoviridae-hMPV is an enveloped negative-sense RNA virus. Viruses within this family encode three surface-expressed membrane proteins. For hMPV these are the small hydrophobic (SH), attachment (G), and fusion (F) proteins (Shafagati & Williams, 2018).

As a class I viral fusion glycoprotein, hMPV F is first translated as a single polypeptide precursor ($F_0$). Proteolytic cleavage converts $F_0$ into disulfide-linked $F_2$ and $F_1$ subunits (FIG. 1A). Three $F_2/F_1$ heterodimers then associate into a metastable prefusion trimer that constitutes the active form of the protein. In cell culture, this proteolytic activation can be accomplished by the addition of trypsin, which cleaves the protein at a monobasic cleavage site (van den Hoogen et al., 2001; Skiadopoulos et al., 2006; Schickli et al., 2005). During natural infection, hMPV $F_0$ is cleaved by trypsin-like extracellular serine proteases, such as TMPRSS2, although the extent to which this occurs in the producing cells versus target cells is not well defined (Shirogane et al., 2008). The N-terminus of the mature $F_1$ subunit contains a hydrophobic sequence called the fusion peptide, which is situated within the internal cavity of the prefusion F trimer (Battles et al., 2017). For other class I fusion proteins, such as human respiratory syncytial virus F (RSV F) and influenza hemagglutinin (HA), it has been shown that the trimer is labile and can transiently splay open, or "breathe" (Bangaru et al., 2019; Watanabe et al., 2019; Gilman et al., 2019). Recently a human antibody targeting the trimer interface of hMPV F has been described, suggesting that prefusion hMPV F undergoes this transient opening in vivo (Huang et al., 2020). To facilitate membrane fusion, the metastable prefusion F protein undergoes a substantial conformational change, liberating and extending the fusion peptide into the host-cell membrane. This unstable pre-hairpin intermediate collapses back onto itself to form a highly stable six-helix bundle composed of a trimer of the N-terminal and C-terminal heptad repeats (HRA and HRB, respectively) in what is termed the postfusion conformation (Más et al., 2016). Given its critical role in viral entry, vaccine candidates for hMPV generally include the F protein. In other words, a potential vaccination strategy for hMPV is through targeting its fusion (F) glycoprotein which is critical for viral infection. However, there remains a need for stabilized F proteins that could be used for identifying drug candidates and for stimulating an effective immune response to the F protein.

SUMMARY

As such, provided herein are thermostable hMPV F prefusion conformation variants. Introduction of paired cystine mutations to introduce disulfide bonds improved expression and thermostability of the protein. Individual hydrophobic, electrostatic interaction, and charge reduction mutations are also beneficial. In addition, combining multiple beneficial mutations further improved the desired protein characteristics.

In one embodiment, provided herein are engineered proteins comprising metapneumovirus (MPV) F protein ectodomains having at least 90% identity to (i) amino acids 19-489 of any of SEQ ID NOs: 1, 2, and 4-7, or (ii) amino acids 19-484 of SEQ ID NO: 3, said engineered proteins comprising at least one mutation relative to the sequence of any one of SEQ ID NOs: 1-7, said at least one mutation comprising a substitution at a position corresponding to: K166, N342, A/D185, K188, T49, V262, H435, E26, G439, N46, L158, A161, L50, V162, E51, R163, V104, N457, L110, N322, A113, D336, A116, A338, A140, A147, S291, S443, S293, S444, S355, V442, T365, V463, S22, G53, V169, E305, L302, V47, A159, T127, N153, G121, I/F258, G106, A107, T160, I128, A190, V118, Q426, L165, V191, S149, I137, V/I122, S192, T317, L105, L134, A117, S347, G261, I268, S470, L473, S265, L460, F48, Q455, V231, A374, I217, S376, G366, S194, L219 A344, A86, T114, V148, D461, L66, L73, N145, Q195, E453, and/or H368. In some aspects, the engineered proteins have at least 95% identity to (i) amino acids 19-489 of any of SEQ ID NOs: 1, 2, and 4-7, or (ii) amino acids 19-484 of SEQ ID NO: 3. SEQ ID NO: 1 corresponds to the BV-115 variant sequence. SEQ ID NO: 2 corresponds to the JSM-1147 variant sequence. SEQ ID NO: 3 corresponds to the DW-1 variant sequence. SEQ ID NO: 4 corresponds to the hMPV A1 NL/1/00 strain F protein (GenBank: AAK62968.2). SEQ ID NO: 5 corresponds to the hMPV A2 NL/00/17 strain F protein (GenBank: ACJ70115.1). SEQ ID NO: 6 corresponds to the hMPV B1 NL/1/99 strain F protein (GenBank: AY525843.1). SEQ ID NO: 7 corresponds to the hMPV B2 TN/99/419 strain F protein (GenBank: AAS92882.1).

In some aspects, the engineered proteins comprise a proline substitution corresponding to A/D185P. In some aspects, the engineered proteins comprise a substitution corresponding to RQSR (residues 99-102 of any one of SEQ ID NOs: 4-7; SEQ ID NO: 9) to RRRR (residues 99-102 of any one of SEQ ID NO: 1-3; SEQ ID NO: 10). In some aspects, the engineered proteins comprise a proline substitution corresponding to A/D185P and a substitution corresponding to RQSR (residues 99-102 of any one of SEQ ID NOs: 4-7; SEQ ID NO: 9) to RRRR (residues 99-102 of any one of SEQ ID NO: 1-3; SEQ ID NO: 10). In some aspects, the engineered proteins comprise a substitution corresponding to residues 87-104 of any one of SEQ ID NOs: 1-7 to GGGGSGGGGSR (SEQ ID NO: 8).

In some aspects, the engineered proteins comprise an engineered disulfide bond comprising paired cysteine substitutions corresponding to: E26C and G439C; N46C and L158C; T49C and A161C; L50C and V162C; E51C and R163C; E51C and K166C; V104C and N457C; L110C and N322C; A113C and D336C; A116C and A338C; A140C and A147C; S291C and S443C; S293C and S443C; S293C and S444C; S355C and V442C; T365C and V463C; S22C and H435C; G53C and K166C; G53C and V169C; E305C and N457C; S291C and L302C; V47C and A159C; T127C and N153C; G121C and I/F258C; F48C and T160C; and/or T365C and Q455C. In some aspects, the engineered proteins comprise an engineered disulfide bond comprising paired cysteine substitutions corresponding to: A116C and A338C; T365C and V463C; T127C and N153C; T365C and Q455C; V104C and N457C; L110C and N322C; or A140C and A147C. In some aspects, the engineered proteins comprise an engineered disulfide bond comprising paired cysteine substitutions corresponding to A140C and A147C. In some aspects, the engineered proteins comprise an engineered disulfide bond comprising paired cysteine substitutions corresponding to V104C and N457C. In some aspects, the engineered proteins comprise an engineered disulfide bond comprising paired cysteine substitutions corresponding to L110C and N322C. In some aspects, the engineered proteins comprise an engineered disulfide bond comprising paired cysteine substitutions corresponding to T365C and V463C.

In some aspects, the engineered proteins comprise a substitution at a position corresponding to L219 and/or V231. In some aspects, the engineered proteins comprise a substitution corresponding to L219K and/or V231I. In some aspects, the engineered proteins comprise paired cysteine substitutions corresponding to T127C and N153C. In some aspects, the engineered proteins comprise paired cysteine substitutions corresponding to L110C and N322C. In some aspects, the engineered proteins comprise paired cysteine substitutions corresponding to A140C and A147C. In some aspects, the engineered proteins comprise a substitution corresponding to G366S.

In some aspects, the engineered proteins comprise a substitution at a position corresponding to Q426, T49, L187, L473 and/or S347. In some aspects, the engineered proteins comprise a substitution corresponding to Q426W, T49E, L187F, L473F and/or S347Q.

In some aspects, the engineered proteins comprise an engineered disulfide bond comprising paired cysteine substitutions corresponding to A116C and A338C. In some aspects, the engineered proteins comprise an engineered disulfide bond comprising paired cysteine substitutions corresponding to T365C and V463C. In some aspects, the engineered proteins comprise an engineered disulfide bond comprising paired cysteine substitutions corresponding to T127C and N153C. In some aspects, the engineered proteins comprise an engineered disulfide bond comprising paired cysteine substitutions corresponding to T365C and Q455C.

In some aspects, the engineered proteins comprise at least one additional engineered disulfide bond.

In some aspects, the engineered proteins comprise a cavity filling substitution at a position corresponding to: G106, A107, T160, L158, I128, A190, V118, Q426, L165, V191, T160, S149, I137, S149, V169, N46, T49, V/I122, S192, T317, V162, L105, L134, A117, S347, V47, G261, I268, S470, V231, A374, I217, and/or S355. In some aspects, the engineered proteins comprise a cavity filling substitution at a position corresponding to: L105, V118, I137, S149, L158, L165 or Q426. In some aspects, the engineered proteins comprise a substitution corresponding to L105I or L105W. In some aspects, the engineered proteins comprise a substitution corresponding to L158W. In some aspects, the engineered proteins comprise a substitution corresponding to V118F or V118M. In some aspects, the engineered proteins comprise a substitution corresponding to Q426W. In some aspects, the engineered proteins comprise a substitution corresponding to L165F. In some aspects, the engineered proteins comprise a substitution corresponding to S149V or S149I. In some aspects, the engineered proteins comprise a substitution at a position corresponding to I137. In some aspects, the engineered proteins comprise a substitution corresponding to I137L.

In some aspects, the engineered proteins comprise a cavity filling substitution selected from the group consisting of: G106W, A107F, T160M, L158W, I128F, A190M, V118F, V118M, Q426W, L165F, V191I, T160V, S149V, I137L, S149I, V169I, N46V, T49I, V/I122L, S192L, T317L, V162F, V162W, L105I, L105F, L105W, L134I, A117M, S347M, S347K, S347Q, V47M, G261M, I268M, S470Y, V231I, A374V, I217V, and/or S355F.

In some aspects, the engineered proteins comprise a proline substitution selected from the group consisting of: A86P, A107P, A113P, T114P, V148P, S443P, D461P, L130P, L141P, K142P, E146P, L151P, N153P, V162P, A/D185P, D186P, L187P, K188P, N342P and A344P.

In some aspects, the engineered proteins comprise a substitution at a position corresponding to S376, G366 and/or S194. In some aspects, the engineered proteins comprise a substitution corresponding to S376T, G366S, and/or S194Q.

In some aspects, the engineered proteins comprise a substitution at a position corresponding to K166. In some aspects, the engineered proteins comprise a substitution corresponding to K166E.

In some aspects, the engineered proteins comprise a substitution modulating pH sensitivity at a position corresponding to H435. In some aspects, the engineered proteins comprise a substitution corresponding to H435E, H435D or H435N.

In some aspects, the engineered proteins comprise an electrostatic interaction substitution at a position corresponding to L66, L73, N145, Q195, E453, L66, K188, H368, D461, T49, and/or V262. In some aspects, the engineered proteins comprise a substitution corresponding to L66N, L73E, N145E, Q195K, E453Q, L66D, K188R, H368R, D461E, T49E, and/or V262D.

In some aspects, the engineered proteins comprise substitutions corresponding to L110C, T127C, A140C, A147C, N153C, L219K, V231I, N322C, T365C, E453Q, and/or V463C.

In some aspects, the engineered proteins comprise substitutions corresponding to T127C, N153C, A185P, T365C, V463C, L219K, and V231I. In some aspects, the engineered proteins comprise substitutions corresponding to T127C, N153C, A185P, T365C, V463C, L219K, V231I, and RQSR (residues 99-102 of any one of SEQ ID NOs: 1-7) to RRRR (SEQ ID NO: 10). In some aspects, the engineered proteins comprise substitutions corresponding to T127C, N153C, T365C, V463C, L219K, and V231I. In some aspects, the engineered protein comprises a polypeptide sequence at least 95%, at least 96%, at least 97%, at least 98%, at least 99%, or 100% identical to SEQ ID NO: 14 or 16.

In some aspects, the engineered proteins comprise substitutions corresponding to L110C, T127C, A140C, A147C, N153C, A185P, L219K, V231I, N322C, T365C, N368H, E453Q, and V463C. In some aspects, the engineered proteins comprise substitutions corresponding to L110C, T127C, A140C, A147C, N153C, A185P, L219K, V231I, N322C, T365C, N368H, E453Q, V463C, and RQSR (residues 99-102 of any one of SEQ ID NOs: 1-7) to RRRR (SEQ ID NO: 10). In some aspects, the engineered proteins comprise substitutions corresponding to L110C, T127C, A140C, A147C, N153C, L219K, V231I, N322C, T365C, N368H, E453Q, and V463C. In some aspects, the engineered protein comprises a polypeptide sequence at least 95%, at least 96%, at least 97%, at least 98%, at least 99%, or 100% identical to SEQ ID NO: 15 or 17.

In some aspects, the engineered proteins comprise a substitution corresponding to residues 87-104 of any one of SEQ ID NOs: 1-7 to GGGGSGGGGSR (SEQ ID NO: 8).

In some aspects, the engineered proteins may comprise any set of substitutions disclosed in Table 1. In some aspects, the engineered proteins may comprise any set of substitutions disclosed in Table 1 in combination with a proline substitution corresponding to A/D185P. In some aspects, the engineered proteins may comprise any set of substitutions disclosed in Table 1 in combination with a substitution corresponding to RQSR (residues 99-102 of any one of SEQ ID NOs: 4-7; SEQ ID NO: 9) to RRRR (residues 99-102 of any one of SEQ ID NOs: 1-3; SEQ ID NO: 10). In some aspects, the engineered proteins may comprise any set of substitutions disclosed in Table 1 in combination with a proline substitution corresponding to A/D185P and a substitution corresponding to RQSR (residues 99-102 of any one of SEQ ID NOs: 4-7; SEQ ID NO: 9) to RRRR (residues 99-102 of any one of SEQ ID NOs: 1-3; SEQ ID NO: 10).

In some aspects, the engineered proteins comprise a combination of at least one engineered disulfide bond, at least one cavity filling substitution and at least one proline substitution.

In some aspects, the engineered proteins have at least 95% identity to the amino acid sequences of any one of SEQ ID NOs: 1-3. In some aspects, the engineered hMPV F protein ectodomains have 95% identity to SEQ ID NO: 3.

In some aspects, the engineered proteins are fused or conjugated to a trimerization domain. In some aspects, the engineered proteins are fused or conjugated to a trimerization domain. In some aspects, the trimerization domain comprises a T4 fibritin trimerization domain.

In some aspects, the engineered proteins are fused or conjugated to a transmembrane domain. In some aspects, the engineered proteins are fused to a transmembrane domain. In some aspects, the transmembrane domain comprises a metapneumovirus (MPV) F protein transmembrane domain.

In some aspects, the engineered proteins comprise an N-terminal signal sequence. In some aspects, the N-terminal signal sequence is MSWKVMIIISLLITPQHG (residues 1-18 of SEQ ID NO: 6 or 7; SEQ ID NO: 11). In some aspects, the N-terminal signal sequence is MSWKVVIIFSL-LITPQHG (residues 1-18 of any one of SEQ ID NOs: 1-5).

In one embodiment, provided herein are engineered metapneumovirus (MPV) F protein trimers comprising at least one subunit according to any one of the present engineered protein embodiments. In some aspects, the trimers are stabilized in a prefusion conformation relative to a trimer of wildtype metapneumovirus (MPV) F subunits. In some aspects, the trimers comprise at least one engineered disulfide bond between subunits. In some aspects, the at least one engineered disulfide bond between subunits is formed by substitutions corresponding to S316C and D421C.

In one embodiment, provided herein are pharmaceutical compositions comprising a pharmaceutically acceptable carrier; and (i) an engineered protein of any one of the present engineered protein embodiments, or (ii) an engineered trimer of any one of the engineered trimer embodiments. In some aspects, the pharmaceutical compositions further comprise an adjuvant.

In one embodiment, provided herein are nucleic acid molecules comprising a nucleotide sequence that encodes an amino acid sequence of an engineered protein of any one of the present engineered protein embodiments. In some aspects, the nucleic acids comprise a DNA expression vector. In some aspects, the nucleic acids comprise an mRNA.

In one embodiment, provided herein are methods of preventing metapneumovirus (MPV) infection or a disease associate with metapneumovirus infection in a subject, comprising administering to the subject an effective amount of the pharmaceutical composition of any one of the present pharmaceutical composition embodiments or a nucleic acid molecule of any one of the present nucleic acid molecule embodiments.

In one embodiment, provided herein are compositions comprising an engineered protein of any one of the present embodiments bound to an antibody.

Other objects, features, and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-B. Beneficial substitutions for hMPV F stabilization. (FIG. 1A) Schematics of the ectodomain of hMPV F protein. The disulfide linkages and the N-glycosylation sites are highlighted. The residue numbers indicating the beginning and the end of F1 and F2 are shown under the bars. (FIG. 1B) Side view of the trimeric hMPV F ectodomain in a prefusion conformation (PDB ID: 5WB0). One protomer is shown as a ribbon diagram, and the other two are shown as a white molecular surface. Each inset corresponds to the antigenic sites where the substitutions are located.

(FIG. 2A) Relative expression of purified individual variants, calculated by area under curve (AUC) of peak fraction of SEC. Variants are grouped by design. The horizontal dotted line indicates the calculated AUC concentration of base construct, which is normalized to 100% for comparison. (FIG. 2B) Size exclusion chromatography (SEC) of purified F variants, grouped by design (proline, polar, cavity filling and disulfide). A vertical dotted line indicates the peak retention volume for hMPV F base construct. (FIG. 2C) Differential scanning fluorimetry (DSF) analysis of thermostability of disulfide variants. The vertical dotted line indicates the melting temperature for base construct. (FIG. 2D) SDS-PAGE analysis of hMPV F base construct and single-substitution F variants. Molecular weight standards are indicated at the left in kDa.

(FIG. 3A) cavity mutations, (FIG. 3B) disulfide mutations, (FIG. 3C) proline mutations, and (FIG. 3D) electrostatic mutations. Molecular weight standards are indicated at the left in kDa.

FIGS. 4A-F. Characterization of multiple-substitution hMPV F variants. (FIGS. 4A-C) SEC of purified multiple-substitution hMPV F variants from three cycles of iterations. A vertical dotted line indicates the peak retention volume for hMPV F base construct. (FIG. 4D) DSF analysis of thermostability of multiple-substitution F variants. The vertical dotted line indicates the melting temperature for base construct. (FIG. 4E) SEC trace of DS-CavEs2 purified from a 1 L culture of FreeStyle 293-F cells. (FIG. 4F) Binding of heat-treated or long-term storage of DS-CavEs2 to MPE8 Fab measured by biolayer interferometry. A vertical dotted line indicates the end of the association event. Untreated DS-CavEs2 was included as a control.

(FIG. 7A) Side view of the atomic model of hMPV F variant (DSx2) bound to a MPE8 Fab, shown as a ribbon diagram. The constant region of MPE8 Fab is omitted for clarity. Side chains of two disulfide substitutions in DSx2 are highlighted in sticks. (FIG. 7B) Zoomed view of the binding interface of the MPE8 light chain CDRs and the antigenic site II/V of F protein. (FIG. 7C) Zoomed view of the binding interface of the MPE8 heavy chain CDRs and F. Main chains of CDR3 packed against antigenic site III which is highlighted as a transparent surface. The key residues that forms polar interactions are shown in sticks.

(FIG. 8A) Side view of the atomic model of apo hMPV F variant (DS-CavEs2) in a prefusion conformation. The model (fire brick ribbon) is superimposed with a prefusion F structure (silver ribbon, PDB ID: 5WB0). The side chains of the introduced substitutions are highlighted in sticks. Each inset corresponds to the antigenic sites which the superimposition is performed. (FIG. 8B) Representative 2D class averages of DS-CavEs2 complexed with MPE8 Fab.

FIG. 9. Structural comparison of hMPV F DSx2 to related PDB structures 5WB0. Superimposition of a single protomer from PDBID: 5WB0 (hMPV F) and hMPV F DSx2.

DETAILED DESCRIPTION

Figure 2A:
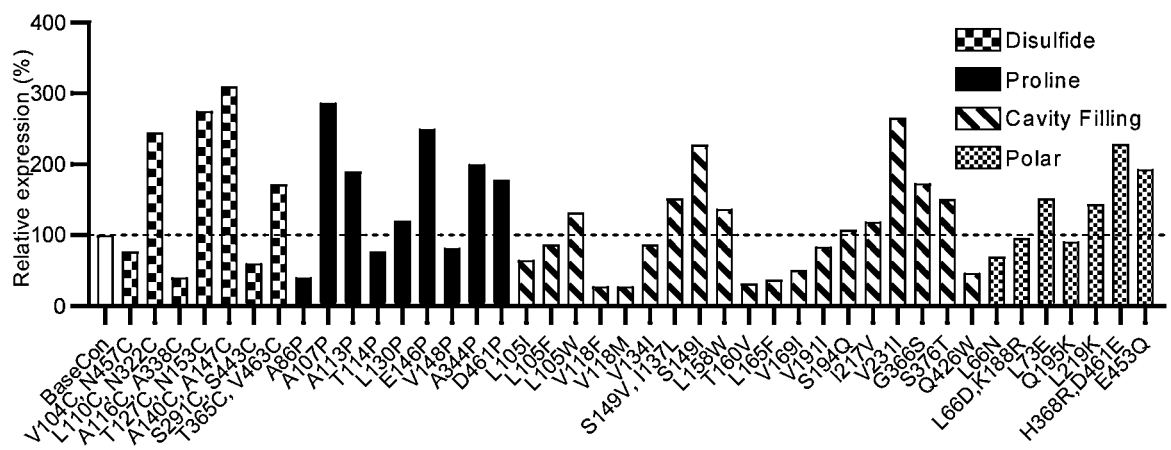
FIGS. 2A-D. Characterization of single-substitution hMPV F variants.

The human metapneumovirus (hMPV) fusion (F) protein is essential for viral entry and is a key target of neutralizing antibodies and vaccine development. The prefusion conformation is thought to be the optimal vaccine antigen, but previously described prefusion F proteins expressed poorly and were not well stabilized. Here, structures of hMPV F were used to guide the design and characterize engineered hMPV F proteins. In some aspects, engineered hMPV F proteins of the embodiments are stabilized in a conformation present before membrane fusions. Such engineered proteins can be used, for example, to stimulate an anti-hMPV F protein specific immune response. In further aspects, engineered F proteins can be used to detect F protein binding antibodies in a sample. Thus, the engineered proteins provided herein allow for more effective methods for vaccination against hMPV as well as enabling new assay methods for detecting anti-hMPV F protein antibodies in, e.g., biological samples.

I. Aspects of the Present Disclosure hMPV F protein, resembling other class I fusion proteins, is readily triggered by the host factors and transitions from metastable prefusion state to highly stable postfusion state. Using prefusion stabilized protein as a vaccinogen, such as DS-Cav1, has proved to trigger higher neutralization titers in animal models compared to using postfusion protein. This inspired use of the prefusion structure of hMPV F (PDB ID: 5WB0) as a guide to strategically introduce mutations, one at a time, specifically to the regions experiencing substantial conformational changes during the pre-to-post transition. Like the recent success on engineering SARS-CoV-2 spikes, multiple proline substitutions increased protein expression while retaining F in prefusion conformation. The role of A107P at fusion peptide is fairly similar to that of F817P substitution from HexaPro (Hsieh et al., 2020), likely by imposing rigidity to fusion peptides and also capping the helices at prefusion conformation. Interestingly, replacing Ala with Phe, an equivalent residue on RSV F, slightly decreased the protein expression relative to the base construct (Table 1). D461P at HRB might also serve as the same function as A107P or A113P, which were the most effective proline substitutions within the fusion peptide. There are three proline substitutions at antigenic site V leading to increases in protein yield. Given that sidechains of these residues are partially exposed on the surface of the trimer, they are considered suboptimal for vaccine antigens.

Implementation of an inter-protomer or inter-subunit salt bridge tends to efficiently hold the trimeric viral protein in a relatively compact conformation, in a more effective way than intra-protomer salt bridges. For example, K588E mutation from gp41 electrostatically interacted with K62 or K492 from gp120, which favors HIV-1 Env to stay in prefusion, closed conformation (Rutten et al., 2018). Among the present designs, L219K substitution from F1 subunit could form a salt bridge with either E80 from the F2 subunit or D209 from the F1 subunit; 73E substitution from F2 subunit could also form a salt bridge with R198 from the neighboring F1 subunit. Both variants boost the expression and have longer retention time in SEC, implicating a strikingly similar role of the salt bridge designs for class I fusion protein. On the other hand, intra-protomer salt bridge design, such as the variant N145E, abolished the expression of hMPV F (Table 1). Likewise, this type of salt bridge did not work well for stabilizing SARS-CoV-2 spike. Reduced repulsion caused by charge clusters at protomer interface is another approach to prevent opening of the trimer. A charge cluster (E453/D454) was discovered at the HRB region in proximity to the base of trimer. Therefore, replacing Glu453 with isosteric Gln could reduce charge repulsion caused by negative charged cluster. Resembling E487Q substitution from RSV F or K588F substitution from Ebola GP (McLellan et al., 2013; Rutten et al., 2020), this variant made hMPV F a more compact trimer and retained native quaternary structure, as evidence by the SEC elution profile (FIG. 2B).

The cavity filling approach was also very effective to stabilize loosely packed viral protein at prefusion conformation. For example, S190F substitutions in Cav1 variant nicely fill the cavity between site V and site II; V207L substitutions, with only single $CH_2$ addition, nicely fill the pocket between site φ. One of the variants with the highest expression, V231I, surprisingly located at domain IIIb (site II), the region does not undergo conformational change during the pre-to-post transition. The other two substitutions (S149I, I137L) that boosted the expression both located at domain IIIa (site V), seemingly packing against each other to stabilize highly flexible α2 and β3.

Among the strategies employed to stabilize hMPV F, perhaps introduction of a disulfide bond gives the highest successful rate. The L110C/N322C substitution was designed to trap the fusion peptide in the central cavity, and the T365C/V463C substitution was designed to lock HRB at the membrane proximal region. By sticking fusion peptide or HRB to a region that stays constant during the pre-to-post transition, F protein was retained at prefusion conformation and its thermostability significantly improved. This approach has been successfully used for several class I viral fusion proteins (McLellan et al., 2013; Stewart-Jones et al., 2018; Sanders et al., 2013). The design is reminiscent of DS variant for RSV F and SOSIP for HIV-1 Env. In contrast, T127C/N153C or A140C/A147C substitutions represent a different type of disulfide design strategy. These disulfide bonds are placed in regions that undergo conformational changes (e.g., domain IIIa (site V)), but they appear to stabilize the prefusion state by preventing refolding of HRA near the central helix. This is similar to the Q162C/L168C substitution used for uenza virus 3 F protein (Stewart-Jones et al., 2018), suggesting that this type of disulfide design may be a general approach to stabilize class I viral fusion proteins. They can prevent the refolding of HRA and potentially force it to fold back to prefusion conformation. Similar disulfide design to restrict the local flexibility of secondary structures at the region undergoing conformational changes during the pre-to-post transition has also been applied successfully to SARS-CoV-2 spike. Intriguingly, V104C/N457C substitution prevents F from furin protease digestion, resulting in a single species of $F_0$ on the SDS-PAGE. The furin cleavage site in proximity to fusion peptide could be buried in the central cavity due to the disulfide design. This variant might be practical for protease-free production of vaccine antigen.

Combining multiple beneficial modifications that increase protein expression and stability has proven to be an effective strategy for producing optimized prefusion antigens (Joyce et al., 2016; Krarup et al., 2015; McLellan et al., 2013; Rutten et al., 2020; Rutten et al., 2018; Jiachen et al., 2021; Hsieh et al., 2020). Here, combining multiple beneficial modifications led to one of the best constructs, DS-CavEs2, which includes the design of DiSulfide bonds, CAVity filling and Electrostatic Stabilization. DS-CavEs2, has 10-fold higher protein expression, enhanced thermostability, and retains prefusion epitopes after heat stress and long-term storage at 4° C. Introduction of two disulfide substitutions at site V, a cavity-filling substitution at site II, and another disulfide bond in proximity to the fusion peptide did not perturb the conformation of the membrane distal half of hMPV F (FIG. 8A), which in RSV F harbors the most potent neutralizing epitopes (Graham et al., 2017; Gilman et al., 2016). The T365C/V463C substitution, in contrast, altered the relative position of the α10 helix. However, this membrane proximal region is less likely to be immunogenic, and no neutralizing antibodies that target this region in RSV F have been discovered.

Another version of DS-CavEs2 with the furin site replaced with flexible glycine-serine (GS) linker or polyglycine linker generates a single chain form of prefusion F trimer. In some embodiments, the linker has the sequence GGSGGS (SEQ ID NO: 12) or GGGGGG (SEQ ID NO: 13). Given that no furin protease is required to make this construct recombinantly, the design could be more cost-effective for industrial production of vaccine antigen.

Notably, both the prefusion-stabilized F constructs crystallized as a monomer, even when complexed with MPE8, which recognizes an epitope that spans adjacent protomers. Other groups have also crystallized monomeric hMPV F bound to antibodies recognizing different antigenic sites (Huang et al., 2020; Wen et al., 2012). Given that trimeric F particles were able to be visualized by nsEM (FIG. 8B), these data suggest that hMPV F trimers are in equilibrium with dissociated monomers, even when fused to a trimerization motif. This is consistent with recent results demonstrating that several class I viral fusion proteins undergo trimer opening or "breathing", and naturally occurring antibodies have been isolated that bind to the trimer interface of influenza HA and hMPV F (Bangaru et al., 2019; Watanabe et al., 2019; Gilman et al., 2019).

Prefusion-stabilized class I viral fusion proteins are known to elicit high neutralizing antibody titers in animals and humans, often an order of magnitude higher than those induced by postfusion antigens (Crank et al., 2019; McLellan et al., 2013; Stewart-Jones et al., 2018). Previous studies showed little difference in the immunogenicity of prefusion and postfusion hMPV F proteins (Battles et al., 2017), but those studies were performed with a 10 µg antigen dose and a postfusion F protein that is now known to have been contaminated with some amount of prefusion-like protein that had yet to adopt the postfusion conformation. It is expected that the prefusion-stabilized hMPV F antigens will elicit higher neutralizing antibody titers in mice than the postfusion F protein. These results would be more consistent with other immunogenicity studies of prefusion-stabilized viral proteins than the previous hMPV F study (Crank et al., 2019; van den Hoogen et al., 2002; Stewart-Jones et al., 2018). The stabilized proteins described here should accelerate development of hMPV F vaccine candidates and facilitate isolation of potent and broadly reactive monoclonal antibodies that may be of use for passive prophylaxis of high-risk cohorts.

II. Definitions

It is to be understood that both the foregoing general description and the following detailed description are exemplary and explanatory only and are not restrictive of the invention as claimed. In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise. Also, the use of the term "portion" can include part of a moiety or the entire moiety.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

The term "about" as used herein when referring to a measurable value such as an amount, a temporal duration, and the like, is meant to encompass variations of up to ±10% from the specified value. Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the disclosed subject matter. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

The term "antibody" refers to an intact immunoglobulin of any isotype, or a fragment thereof that can compete with the intact antibody for specific binding to the target antigen, and includes, for instance, chimeric, humanized, fully human, and bispecific antibodies. An "antibody" is a species of an antigen binding protein. An intact antibody will generally comprise at least two full-length heavy chains and two full-length light chains, but in some instances can include fewer chains such as antibodies naturally occurring in camelids which can comprise only heavy chains. Antibodies can be derived solely from a single source, or can be "chimeric," that is, different portions of the antibody can be derived from two different antibodies as described further below. The antigen binding proteins, antibodies, or binding fragments can be produced in hybridomas, by recombinant DNA techniques, or by enzymatic or chemical cleavage of intact antibodies. Unless otherwise indicated, the term "antibody" includes, in addition to antibodies comprising two full-length heavy chains and two full-length light chains, derivatives, variants, fragments, and muteins thereof, examples of which are described below. Furthermore, unless explicitly excluded, antibodies include monoclonal antibodies, bispecific antibodies, minibodies, domain antibodies, synthetic antibodies (sometimes referred to herein as "antibody mimetics"), chimeric antibodies, humanized antibodies, human antibodies, antibody fusions (sometimes referred to herein as "antibody conjugates"), and fragments thereof, respectively. In some embodiments, the term also encompasses peptibodies.

Naturally occurring antibody structural units typically comprise a tetramer. Each such tetramer typically is composed of two identical pairs of polypeptide chains, each pair having one full-length "light" (in certain embodiments, about 25 kDa) and one full-length "heavy" chain (in certain embodiments, about 50-70 kDa). The amino-terminal portion of each chain typically includes a variable region of about 100 to 110 or more amino acids that typically is responsible for antigen recognition. The carboxy-terminal portion of each chain typically defines a constant region that can be responsible for effector function. Human light chains are typically classified as kappa and lambda light chains. Heavy chains are typically classified as mu, delta, gamma, alpha, or epsilon, and define the antibody's isotype as IgM, IgD, IgG, IgA, and IgE, respectively. IgG has several subclasses, including, but not limited to, IgG1, IgG2, IgG3, and IgG4. IgM has subclasses including, but not limited to, IgM1 and IgM2. IgA is similarly subdivided into subclasses including, but not limited to, IgA1 and IgA2. Within full-length light and heavy chains, typically, the variable and constant regions are joined by a "J" region of about 12 or more amino acids, with the heavy chain also including a "D" region of about 10 more amino acids. See, e.g., Fundamental Immunology, Ch. 7 (Paul, W., ed., 2nd ed. Raven Press, N.Y. (1989)) (incorporated by reference in its entirety for all purposes). The variable regions of each light/heavy chain pair typically form the antigen binding site.

The term "variable region" or "variable domain" refers to a portion of the light and/or heavy chains of an antibody, typically including approximately the amino-terminal 120 to 130 amino acids in the heavy chain and about 100 to 110 amino terminal amino acids in the light chain. In certain embodiments, variable regions of different antibodies differ extensively in amino acid sequence even among antibodies of the same species. The variable region of an antibody typically determines specificity of a particular antibody for its target.

The variable regions typically exhibit the same general structure of relatively conserved framework regions (FR) joined by three hyper variable regions, also called complementarity determining regions or CDRs. The CDRs from the two chains of each pair typically are aligned by the framework regions, which can enable binding to a specific epitope. From N-terminal to C-terminal, both light and heavy chain variable regions typically comprise the domains FR1, CDR1, FR2, CDR2, FR3, CDR3 and FR4. The assignment of amino acids to each domain is typically in accordance with the definitions of Kabat Sequences of Proteins of Immunological Interest (National Institutes of Health, Bethesda, Md. (1987 and 1991)), Chothia & Lesk, J. Mol. Biol., 196:901-917 (1987) or Chothia et al., Nature, 342: 878-883 (1989).

In certain embodiments, an antibody heavy chain binds to an antigen in the absence of an antibody light chain. In certain embodiments, an antibody light chain binds to an antigen in the absence of an antibody heavy chain. In certain embodiments, an antibody binding region binds to an antigen in the absence of an antibody light chain. In certain embodiments, an antibody binding region binds to an antigen in the absence of an antibody heavy chain. In certain embodiments, an individual variable region specifically binds to an antigen in the absence of other variable regions.

In certain embodiments, definitive delineation of a CDR and identification of residues comprising the binding site of an antibody is accomplished by solving the structure of the antibody and/or solving the structure of the antibody-ligand complex. In certain embodiments, that can be accomplished by any of a variety of techniques known to those skilled in the art, such as X-ray crystallography. In certain embodiments, various methods of analysis can be employed to identify or approximate the CDR regions. Examples of such methods include, but are not limited to, the Kabat definition, the Chothia definition, the AbM definition and the contact definition.

The Kabat definition is a standard for numbering the residues in an antibody and is typically used to identify CDR regions. See, e.g., Johnson & Wu, Nucleic Acids Res., 28: 214-8 (2000). The Chothia definition is similar to the Kabat definition, but the Chothia definition takes into account positions of certain structural loop regions. See, e.g., Chothia et al., J. Mol. Biol., 196: 901-17 (1986); Chothia et al., Nature, 342: 877-83 (1989). The AbM definition uses an integrated suite of computer programs produced by Oxford Molecular Group that model antibody structure. See, e.g., Martin et al., Proc Natl Acad Sci (USA), 86:9268-9272 (1989); "AbM™, A Computer Program for Modeling Variable Regions of Antibodies," Oxford, UK; Oxford Molecular, Ltd. The AbM definition models the tertiary structure of an antibody from primary sequence using a combination of knowledge databases and ab initio methods, such as those described by Samudrala et al., "Ab Initio Protein Structure Prediction Using a Combined Hierarchical Approach," in PROTEINS, Structure, Function and Genetics Suppl., 3:194-198 (1999). The contact definition is based on an analysis of the available complex crystal structures. See, e.g., MacCallum et al., J. Mol. Biol., 5:732-45 (1996).

By convention, the CDR regions in the heavy chain are typically referred to as H1, H2, and H3 and are numbered sequentially in the direction from the amino terminus to the carboxy terminus. The CDR regions in the light chain are typically referred to as L1, L2, and L3 and are numbered sequentially in the direction from the amino terminus to the carboxy terminus.

The term "light chain" includes a full-length light chain and fragments thereof having sufficient variable region sequence to confer binding specificity. A full-length light chain includes a variable region domain, VL, and a constant region domain, CL. The variable region domain of the light chain is at the amino-terminus of the polypeptide. Light chains include kappa chains and lambda chains.

The term "heavy chain" includes a full-length heavy chain and fragments thereof having sufficient variable region sequence to confer binding specificity. A full-length heavy chain includes a variable region domain, VH, and three constant region domains, CH1, CH2, and CH3. The VH domain is at the amino-terminus of the polypeptide, and the CH domains are at the carboxyl-terminus, with the CH3 being closest to the carboxy-terminus of the polypeptide. Heavy chains can be of any isotype, including IgG (including IgG1, IgG2, IgG3 and IgG4 subtypes), IgA (including IgA1 and IgA2 subtypes), IgM and IgE.

A bispecific or bifunctional antibody typically is an artificial hybrid antibody having two different heavy/light chain pairs and two different binding sites. Bispecific antibodies can be produced by a variety of methods including, but not limited to, fusion of hybridomas or linking of Fab' fragments. See, e.g., Songsivilai et al., Clin. Exp. Immunol., 79: 315-321 (1990); Kostelny et al., J. Immunol., 148:1547-1553 (1992).

The term "antigen" refers to a substance capable of inducing adaptive immune responses. Specifically, an antigen is a substance which serves as a target for the receptors of an adaptive immune response. Typically, an antigen is a molecule that binds to antigen-specific receptors but cannot induce an immune response in the body by itself. Antigens are usually proteins and polysaccharides, less frequently also lipids. As used herein, antigens also include immunogens and haptens.

An "Fc" region comprises two heavy chain fragments comprising the CH1 and CH2 domains of an antibody. The two heavy chain fragments are held together by two or more disulfide bonds and by hydrophobic interactions of the CH3 domains.

The "Fv region" comprises the variable regions from both the heavy and light chains but lacks the constant regions.

An antibody that "specifically binds to" or is "specific for" a particular polypeptide or an epitope on a particular polypeptide is one that binds to that particular polypeptide or epitope on a particular polypeptide without substantially binding to any other polypeptide or polypeptide epitope. For example, the hMPV F protein specific antibodies of the present invention are specific to hMPV F protein. In some embodiments, the antibody that binds to hMPV F protein has a dissociation constant (Kd) of ≤100 nM, ≤10 nM, ≤1 nM, ≤0.1 nM, ≤0.01 nM, or ≤0.001 nM (e.g., 10-8M or less, e.g., from 10-8M to 10-13M, e.g., from 10-9M to 10-13 M).

The term "compete" when used in the context of antigen binding proteins (e.g., antibody or antigen-binding fragment thereof) that compete for the same epitope means competition between antigen binding proteins as determined by an assay in which the antigen binding protein (e.g., antibody or antigen-binding fragment thereof) being tested prevents or inhibits (e.g., reduces) specific binding of a reference antigen binding protein (e.g., a ligand, or a reference antibody) to a common antigen (e.g., hMPV F or a fragment thereof). Numerous types of competitive binding assays can be used to determine if one antigen binding protein competes with another, for example: solid phase direct or indirect radio-immunoassay (RIA), solid phase direct or indirect enzyme immunoassay (EIA), sandwich competition assay (see, e.g., Stahli et al., 1983, Methods in Enzymology 9:242-253); solid phase direct biotin-avidin EIA (see, e.g., Kirkland et al., 1986, J. Immunol. 137:3614-3619) solid phase direct labeled assay, solid phase direct labeled sandwich assay (see, e.g., Harlow and Lane, 1988, Antibodies, A Laboratory Manual, Cold Spring Harbor Press); solid phase direct label RIA using 1-125 label (see, e.g., Morel et al., 1988, Molec. Immunol. 25:7-15); solid phase direct biotin-avidin EIA (see, e.g., Cheung, et al., 1990, Virology 176:546-552); and direct labeled RIA (Moldenhauer et al., 1990, Scand. J. Immunol. 32:77-82). Typically, such an assay involves the use of purified antigen bound to a solid surface or cells bearing either of these, an unlabeled test antigen binding protein and a labeled reference antigen binding protein. Competitive inhibition is measured by determining the amount of label bound to the solid surface or cells in the presence of the test antigen binding protein. Usually the test antigen binding protein is present in excess. Antigen binding proteins identified by competition assay (competing antigen binding proteins) include antigen binding proteins binding to the same epitope as the reference antigen binding proteins and antigen binding proteins binding to an adjacent epitope sufficiently proximal to the epitope bound by the reference antigen binding protein for steric hindrance to occur. Additional details regarding methods for determining competitive binding are provided in the examples herein. Usually, when a competing antigen binding protein is present in excess, it will inhibit (e.g., reduce) specific binding of a reference antigen binding protein to a common antigen by at least 40-45%, 45-50%, 50-55%, 55-60%, 60-65%, 65-70%, 70-75% or 75% or more. In some instances, binding is inhibited by at least 80-85%, 85-90%, 90-95%, 95-97%, or 97% or more.

The term "epitope" as used herein refers to the specific group of atoms or amino acids on an antigen to which an antibody binds. The epitope can be either linear epitope or a conformational epitope. A linear epitope is formed by a continuous sequence of amino acids from the antigen and interacts with an antibody based on their primary structure. A conformational epitope, on the other hand, is composed of discontinuous sections of the antigen's amino acid sequence and interacts with the antibody based on the 3D structure of the antigen. In general, an epitope is approximately five or six amino acid in length. Two antibodies may bind the same epitope within an antigen if they exhibit competitive binding for the antigen.

The term "host cell" means a cell that has been transformed, or is capable of being transformed, with a nucleic acid sequence and thereby expresses a gene of interest. The term includes the progeny of the parent cell, whether or not the progeny is identical in morphology or in genetic make-up to the original parent cell, so long as the gene of interest is present.

The term "identity" refers to a relationship between the sequences of two or more polypeptide molecules or two or more nucleic acid molecules, as determined by aligning and comparing the sequences. "Percent identity" means the percent of identical residues between the amino acids or nucleotides in the compared molecules and is calculated based on the size of the smallest of the molecules being compared. For these calculations, gaps in alignments (if any) are preferably addressed by a particular mathematical model or computer program (i.e., an "algorithm"). Methods that can be used to calculate the identity of the aligned nucleic acids or polypeptides include those described in Computational Molecular Biology, (Lesk, A. M., ed.), 1988, New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., 1987, Sequence Analysis in Molecular Biology, New York: Academic Press; Sequence Analysis Primer, (Gribskov, M. and Devereux, J., eds.), 1991, New York: M. Stockton Press; and Carillo et al., 1988, SIAM J. Applied Math. 48:1073.

In calculating percent identity, the sequences being compared are typically aligned in a way that gives the largest match between the sequences. One example of a computer program that can be used to determine percent identity is the GCG program package, which includes GAP (Devereux et al., 1984, Nucl. Acid Res. 12:387; Genetics Computer Group, University of Wisconsin, Madison, Wis.). The computer algorithm GAP is used to align the two polypeptides or polynucleotides for which the percent sequence identity is to be determined. The sequences are aligned for optimal matching of their respective amino acid or nucleotide (the "matched span", as determined by the algorithm). A gap opening penalty (which is calculated as 3× the average diagonal, wherein the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. In certain embodiments, a standard comparison matrix (see, Dayhoff et al., 1978, Atlas of Protein Sequence and Structure 5:345-352 for the PAM 250 comparison matrix; Henikoff et al., 1992, Proc. Natl. Acad. Sci. U.S.A. 89:10915-10919 for the BLOSUM 62 comparison matrix) is also used by the algorithm.

Examples of parameters that can be employed in determining percent identity for polypeptides or nucleotide sequences using the GAP program can be found in Needleman et al., 1970, J. Mol. Biol. 48:443-453.

Certain alignment schemes for aligning two amino acid sequences may result in matching of only a short region of the two sequences, and this small aligned region may have very high sequence identity even though there is no significant relationship between the two full-length sequences. Accordingly, the selected alignment method (GAP program) can be adjusted if so desired to result in an alignment that spans at least 50 or other number of contiguous amino acids of the target polypeptide.

The term "link" as used herein refers to the association via intramolecular interaction, e.g., covalent bonds, metallic bonds, and/or ionic bonding, or inter-molecular interaction, e.g., hydrogen bond or noncovalent bonds.

The term "operably linked" refers to an arrangement of elements wherein the components so described are configured so as to perform their usual function. Thus, a given signal peptide that is operably linked to a polypeptide directs the secretion of the polypeptide from a cell. In the case of a promoter, a promoter that is operably linked to a coding sequence will direct the expression of the coding sequence. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

The term "polynucleotide" or "nucleic acid" includes both single-stranded and double-stranded nucleotide polymers. The nucleotides comprising the polynucleotide can be ribonucleotides or deoxyribonucleotides or a modified form of either type of nucleotide. Said modifications include base modifications such as bromouridine and inosine derivatives, ribose modifications such as 2',3'-dideoxyribose, and inter-nucleotide linkage modifications such as phosphorothioate, phosphorodithioate, phosphoroselenoate, phosphorodiselenoate, phosphoroanilothioate, phoshoraniladate and phosphoroamidate.

As used herein, a "vector" refers to a nucleic acid molecule as introduced into a host cell, thereby producing a transformed host cell. A vector may include nucleic acid sequences that permit it to replicate in the host cell, such as an origin of replication. A vector may also include one or more therapeutic genes and/or selectable marker genes and other genetic elements known in the art. A vector can transduce, transform or infect a cell, thereby causing the cell to express nucleic acids and/or proteins other than those native to the cell. A vector optionally includes materials to aid in achieving entry of the nucleic acid into the cell, such as a viral particle, liposome, protein coating or the like.

The terms "polypeptide" or "protein" means a macromolecule having the amino acid sequence of a native protein, that is, a protein produced by a naturally-occurring and non-recombinant cell; or it is produced by a genetically-engineered or recombinant cell, and comprise molecules having the amino acid sequence of the native protein, or molecules having deletions from, additions to, and/or substitutions of one or more amino acids of the native sequence. The term also includes amino acid polymers in which one or more amino acids are chemical analogs of a corresponding naturally occurring amino acid and polymers. The terms "polypeptide" and "protein" specifically encompass hMPV F protein binding proteins, antibodies, or sequences that have deletions from, additions to, and/or substitutions of one or more amino acid of antigen-binding protein. The term "polypeptide fragment" refers to a polypeptide that has an amino-terminal deletion, a carboxyl-terminal deletion, and/or an internal deletion as compared with the full-length native protein. Such fragments can also contain modified amino acids as compared with the native protein. In certain embodiments, fragments are about five to 500 amino acids long. For example, fragments can be at least 5, 6, 8, 10, 14, 20, 50, 70, 100, 110, 150, 200, 250, 300, 350, 400, or 450 amino acids long. Useful polypeptide fragments include immunologically functional fragments of antibodies, including binding domains. In the case of a hMPV F protein-binding antibody, useful fragments include but are not limited to a CDR region, a variable domain of a heavy and/or light chain, a portion of an antibody chain or just its variable region including two CDRs, and the like.

The pharmaceutically acceptable carriers useful in this invention are conventional. Remington's Pharmaceutical Sciences, by E. W. Martin, Mack Publishing Co., Easton, PA, 15th Edition (1975), describes compositions and formulations suitable for pharmaceutical delivery of the fusion proteins herein disclosed. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

The term "therapeutically effective amount" or "effective dosage" as used herein refers to the dosage or concentration of a drug effective to treat a disease or condition. For example, with regard to the use of the monoclonal antibodies or antigen-binding fragments thereof disclosed herein to treat viral infection.

"Treating" or "treatment" of a condition as used herein includes preventing or alleviating a condition, slowing the onset or rate of development of a condition, reducing the risk of developing a condition, preventing or delaying the development of symptoms associated with a condition, reducing or ending symptoms associated with a condition, generating a complete or partial regression of a condition, curing a condition, or some combination thereof.

III. The hMPV F Protein

Human metapneumovirus (hMPV) is a negative-sense enveloped virus of the Pneumoviridae family and was discovered in 2001 but has been circulating for at least a half century before its discovery. The hMPV fusion (F) protein is one of three surface glycoproteins encoded by the viral genome. As a class I fusion, hMPV F is first translated as a single polypeptide precursor (F0). Initially nonfunctional, a proteolytic cleavage event is necessary to form the F1 and F2 subunits which are covalently linked by disulfide bonds. The new N-terminus of the F2 polypeptide contains a hydrophobic sequence which gets inserted into the host-cell membrane during the process that eventually fuses the viral and host-cell membranes. At some point, either in transit or at the membrane surface, the F protein associates with itself to form a metastable trimer in what is termed to be the prefusion conformation. The hMPV fusion protein is cleaved extracellularly by a trypsin-like protease. An unknown triggering event occurs that influences the F protein to undergo a dramatic conformational change, extending the fusion peptide into the host-cell membrane, before collapsing back onto itself to form a six-helix bundle in what is termed the postfusion conformation. The energy differential between the elongated intermediate and the postfusion conformation provides the energy necessary for membrane fusion.

Historically the structures of the paramyxovirus fusion proteins have been divided into domains generally segmenting the first solved prefusion protein into a head, neck, and stalk. The nomenclature of assigning three general domains (DI, DII, and DIII) to the prefusion structures of additional structures has continued. Since the pneumoviridae family was previously a subfamily of the paramyxoviruses, they too retain this convention. The domains of hMPV are vaguely broken into the same three domains with an additional two regions of heptad repeats defined as well. Heptad repeat A (HRA) is at the N-terminus of F1 located within DIIIa and heptad repeat B is at the C-terminus outside of the defined domain regions and prior to the transmembrane domain of the protein. However, transferring the antigenic site nomenclature used for the respiratory syncytial virus (RSV), another member of the pneumoviridae family, fusion protein can be used for a more precise description of protein areas due to their structural similarity. DIIIa experiences the largest conformational rearrangement when the fusion peptide is released from the internal cavity of the trimer and HRA forms a three-coil bundle as the fusion peptide is inserted into the target membrane. HRB eventually associates around the outside of the HRA bundle to form the 6HB in the postfusion conformation.

Stabilization of class I fusion proteins in their prefusion conformation has recently produced promising results as vaccine antigens in clinical trials, with both RSV and SARS-Coronavirus-2 vaccines using this approach (Baden et al., 2020; Keech et al., 2020; Williams et al., 2020; Crank et al., 2019). RSV shares ~33% sequence identity with hMPV, and the two prefusion structures are highly similar (Battles et al., 2017; van den hoogen et al., 2002). Based on its solved prefusion structure, a few different strategies have been used to stabilize RSV F in its prefusion conformation, including the introduction of prolines, disulfide bonds, and cavity-filling substitutions (Joyce et al., 2016; Krarup et al., 2015; McLellan et al., 2013). For DS-Cav1, internal cavities were filled more optimally by hydrophobic residue substitutions, and the introduction of a disulfide bond was introduced into the fusion peptide region. For PR-DM, a proline residue was introduced to prevent a loop region from rearranging into the extended alpha helix seen in the postfusion conformation. In RSV F areas of charge repulsion were also identified and reduced. Similarly, a solved prefusion structure allowed for the stabilization of coronaviruses by introducing two proline substitutions (S-2P) into a hinge region. There are also examples within the HIV (SOSIP) and influenza field where engineering stabilizing mutations have resulted in well behaved prefusion reagents.

Recently, knowledge gained from RSV F studies was used to stabilize hMPV F in the prefusion conformation. First, the $F_2/F_1$ cleavage site sequence 'RQSR' was substituted with a polybasic 'RRRR' sequence to enable efficient cleavage by furin-like proteases in the producing cell. Then, mimicking an RSV F stabilization strategy (Krarup et al., 2015), a proline was introduced into the helix-loop-helix region in $F_1$ at the membrane-distal trimer apex. This engineering strategy allowed for a trimeric prefusion crystal structure of hMPV F to be obtained, but the protein expressed poorly, suggesting further engineering was needed (Battles et al., 2017). Additionally, previous serum-depletion assays and murine immunization experiments indicated that there were no significant antigenic differences between prefusion and postfusion hMPV F (Battles et al., 2017). In contrast, prefusion RSV F elicits a more robust neutralizing antibody response than postfusion RSV F, and serum-depletion experiments demonstrated that most of the RSV-neutralizing activity in human sera binds exclusively to the prefusion conformation (Sastre et al., 2005; Magro et al., 2012). These data suggested that a more stable prefusion hMPV F construct was needed to investigate these incongruent results.

To this end, F protein stabilizing strategies have been demonstrated herein by mutation of the F protein coding sequence. The published prefusion hMPV F structure was used to guide the engineering of additional amino acid substitutions. Combinations of multiple beneficial substitutions were found to have an additive effect for the desired protein characteristics. Mutations analyzed and provided herein are detailed in Table 1, below. Mutant proteins were expressed as detailed in the Examples and the amount produced protein and trimer complex was determined.

TABLE 1

F protein substitutions and mutations.

| Designation | Mutations (positions relative to any of SEQ ID NOs: 1-7) |
|---|---|
| BV-115 (SEQ ID NO: 1) | A185P/G294E/RQSR (SEQ ID NO: 9) to RRRR (SEQ ID NO: 10) |
| JSM-1147 (SEQ ID NO: 2) | A185P/H368N/RQSR (SEQ ID NO: 9) to RRRR (SEQ ID NO: 10) |
| MM-1 | JSM-1147 + L110C/T127C/N153C/L219K/V231I/N322C/T365C/V463C |
| MM-1H | JSM-1147 + L110C/T127C/N153C/L219K/V231I/N322C/T365C/N368H/V463C |
| MM-4 | JSM-1147 + L110C/T127C/A140C/A147C/N153C/L219K/V231I/N322C/T365C/V463C |
| MM-4H | JSM-1147 + L110C/T127C/A140C/A147C/N153C/L219K/V231I/N322C/T365C/N368H/V463C |
| DS-CavEs (SEQ ID NO: 14) | JSM-1147 + T127C/N153C/L219K/V231I/T365C/V463C |
| DS-CavEs2 (SEQ ID NO: 15) | JSM-1147 + L110C/T127C/A140C/A147C/N153C/L219K/V231I/N322C/T365C/N368H/E453Q/V463C |
| DS-CavEs2 SC | JSM-1147 + L110C/T127C/A140C/A147C/N153C/L219K/V231I/N322C/T365C/E453Q/V463C, residues 87-104 are replaced with GGGGSGGGGSR (SEQ ID NO: 8) |
| SC1 | Residues 87-104 are replaced with GGGGSGGGGSR (SEQ ID NO: 8) |
| DSx2 | JSM-1147 + T127C/N153C/T365C/V463C |
| DSx2/L219K | JSM-1147 + T127C/N153C/L219K/T365C/V463C |
| DSx2/V231I | JSM-1147 + T127C/N153C/V231I/T365C/V463C |
| CL-1 | JSM-1147 + L473F (113C/339C/H368N) |
| CL-2 | JSM-1147 + A117M |
| CL-3 | JSM-1147 + S347M |
| CL-3_2 | JSM-1147 + S347K |
| CL-3_3 | JSM-1147 + S347Q |
| CL-4 | JSM-1147 + V47M |
| CL-5 | JSM-1147 + T49E |
| CL-6 | JSM-1147 + G261M |
| CL-7 | JSM-1147 + I268M |
| CL-8 | JSM-1147 + V262D |
| CL-9 | JSM-1147 + S470Y |
| CL-10 | JSM-1147 + V191F |
| CL-11 | JSM-1147 + S265K |
| CL-12 | JSM-1147 + L460F |
| CL-13 | V118F |
| CL-14 | V118M |
| CL-15 | Q426W |
| CL-16 | L165F |
| CL-21 | L219K/T365C/V463C |
| CL-23 | V231I/T365C/V463C |
| CL-34 | A86P |
| CL-35 | A107P |
| CL-36 | A113P |
| CL-37 | T114P |
| CL-38 | V148P |
| CL-39 | S443P |
| CL-40 | D461P |
| CL-41 | L66N |
| CL-42 | L73E |
| CL-43 | N145E |
| CL-44 | Q195K |
| CL-45 | E453Q |
| CL-46 | L66D/K188R |
| CL-47 | H368R-D461E |
| CL-48 | L219K |
| CL-DS-1 | JSM1147 + F48C-T160C |
| CL-DS-2 | JSM1147 + T365C-Q455C |
| CL-DS-4 | T365C/V463C |
| JM-1 | E26C/G439C |
| JM-2 | N46C/L158C |
| JM-3 | T49C/A161C |
| JM-4 | L50C/V162C |
| JM-5 | E51C/R163C |
| JM-6 | E51C/K166C |
| JM-7 | V104C/N457C |
| JM-8 | L110C/N322C |
| JM-9 | A113C/D336C |
| JM-10 | A113C/D336C, R40M |
| JM-11 | A116C/A338C |
| JM-12 | A140C/A147C |
| JM-13 | S291C/S443C |
| JM-14 | S293C/S443C |
| JM-15 | S293C/S444C |
| JM-16 | S355C/V442C |
| JM-17 | G106W |
| JM-18 | A107F |
| JM-19 | T160M |
| JM-20 | L158W |
| JM-21 | I128F |
| JM-22 | A190M |

TABLE 1-continued

F protein substitutions and mutations.

| Designation | Mutations (positions relative to any of SEQ ID NOs: 1-7) |
|---|---|
| JM-23 | S316C/D421C |
| JM-24 | T160V |
| JM-25 | S149V, I137L |
| JM-26 | S149I |
| JM-27 | V169I |
| JM-28 | N46V |
| JM-29 | T49I |
| JM-30 | V122L |
| JM-31 | S192L |
| JM-32 | T317L |
| JM-33 | N342P |
| JM-34 | E305C/N457C |
| JM-36 | S291C/L302C |
| JM-37 | V47C/A159C |
| JM-38 | T127C/N153C |
| JM-39 | G121C/I258C |
| NW-1 | L130P |
| NW-2 | L141P |
| NW-3 | K142P |
| NW-4 | E146P |
| NW-5 | L151P |
| NW-6 | N153P |
| NW-7 | V162P |
| NW-8 | D186P |
| NW-9 | L187P |
| SR-1 | V162F |
| SR-2 | V162W |
| SR-3 | K188P |
| SR-4 | L105I |
| SR-5 | L105F |
| SR-6 | L105W |
| SR-7 | V134I |
| SR-8 | H435E |
| SR-9 | H435D |
| SR-10 | H435N |
| SR-11 | K166E |
| SR-13 | G53C/K166C |
| SR-14 | G53C/V169C |
| SR-16 | V231I |
| SR-17 | A344P |
| SR-18 | S376T |
| SR-19 | G366S |
| SR-20 | A374V |
| SR-21 | S194Q |
| SR-22 | I217V |
| SR-23 | S355F |
| SR-24 | V191I |

IV. Pharmaceutical Formulations

The present disclosure provides pharmaceutical compositions comprising an engineered hMPV F protein. Such compositions can be used for stimulating an immune response, such as part of vaccine formulation.

In the case that a nucleic acid molecule encoding an engineered hMPV F protein is used in a pharmaceutical composition, the nucleic acid molecule may comprise or consist of deoxyribonucleotides and/or ribonucleotides, or analogs thereof, covalently linked together. A nucleic acid molecule as described herein generally contains phosphodiester bonds, although in some cases, nucleic acid analogs are included that may have at least one different linkage, e.g., phosphoramidate, phosphorothioate, phosphorodithioate, or O-methylphosphoroamidite linkages, and peptide nucleic acid backbones and linkages. Mixtures of naturally occurring polynucleotides and analogs can be made; alternatively, mixtures of different polynucleotide analogs, and mixtures of naturally occurring polynucleotides and analogs may be made. A nucleic acid molecule may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. The term also includes both double- and single-stranded molecules. Unless otherwise specified or required, the term polynucleotide encompasses both the double-stranded form and each of two complementary single-stranded forms known or predicted to make up the double-stranded form. A nucleic acid molecule is composed of a specific sequence of four nucleotide bases: adenine (A), cytosine (C), guanine (G), thymine (T), and uracil (U) for thymine when the polynucleotide is RNA. Thus, the term "nucleic acid sequence" is the alphabetical representation of a nucleic acid molecule. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues.

In some embodiments, the nucleic acids of the present disclosure comprise one or more modified nucleosides comprising a modified sugar moiety. Such compounds comprising one or more sugar-modified nucleosides may have desirable properties, such as enhanced nuclease stability or increased binding affinity with a target nucleic acid relative to an oligonucleotide comprising only nucleosides comprising naturally occurring sugar moieties. In some embodiments, modified sugar moieties are substituted sugar moieties. In some embodiments, modified sugar moieties are sugar surrogates. Such sugar surrogates may comprise one or more substitutions corresponding to those of substituted sugar moieties.

In some embodiments, modified sugar moieties are substituted sugar moieties comprising one or more non-bridging sugar substituent, including but not limited to substituents at the 2' and/or 5' positions. Examples of sugar substituents suitable for the 2'-position, include, but are not limited to: 2'-F, 2'-OCH3 ("OMe" or "O-methyl"), and 2'-O(CH$_2$)$_2$OCH$_3$ ("MOE"). In certain embodiments, sugar substituents at the 2' position is selected from allyl, amino, azido, thio, O-allyl, O—C$_1$-C$_{10}$ alkyl, O—C$_1$-C$_{10}$ substituted alkyl; OCF$_3$, O(CH$_2$)$_2$SCH$_3$, O(CH$_2$)$_2$—O—N(Rm)(Rn), and O—CH$_2$—C(=O)—N(Rm)(Rn), where each Rm and Rn is, independently, H or substituted or unsubstituted C$_1$-C$_{10}$ alkyl. Examples of sugar substituents at the 5'-position, include, but are not limited to: 5'-methyl (R or S); 5'-vinyl, and 5'-methoxy. In some embodiments, substituted sugars comprise more than one non-bridging sugar substituent, for example, T-F-5'-methyl sugar moieties (see, e.g., PCT International Application WO 2008/101157, for additional 5',2'-bis substituted sugar moieties and nucleosides).

Nucleosides comprising 2'-substituted sugar moieties are referred to as 2'-substituted nucleosides. In some embodiments, a 2'-substituted nucleoside comprises a 2'-substituent group selected from halo, allyl, amino, azido, SH, CN, OCN, CF$_3$, OCF$_3$, O, S, or N(Rm)-alkyl; O, S, or N(Rm)-alkenyl; O, S or N(Rm)-alkynyl; O-alkylenyl-O-alkyl, alkynyl, alkaryl, aralkyl, O-alkaryl, O-aralkyl, O(CH$_2$)$_2$SCH$_3$, O(CH$_2$)$_2$—O—N(Rm)(Rn) or O—CH$_2$—C(=O)—N(Rm) (Rn), where each Rm and Rn is, independently, H, an amino protecting group or substituted or unsubstituted C$_1$-C$_{10}$ alkyl. These 2'-substituent groups can be further substituted with one or more substituent groups independently selected from hydroxyl, amino, alkoxy, carboxy, benzyl, phenyl, nitro ($NO_2$), thiol, thioalkoxy (S-alkyl), halogen, alkyl, aryl, alkenyl and alkynyl.

In some embodiments, a 2'-substituted nucleoside comprises a 2'-substituent group selected from F, $NH_2$, $N_3$, $OCF_3$, O—$CH_3$, $O(CH_2)_3NH_2$, $CH_2$—CH═$CH_2$, O—$CH_2$—CH═$CH_2$, $OCH_2CH_2OCH_3$, $O(CH_2)_2SCH_3$, O—$(CH_2)_2$—O—N(Rm)(Rn), $O(CH_2)_2O(CH_2)_2N(CH_3)_2$, and N-substituted acetamide (O—$CH_2$—C(═O)—N(Rm)(Rn) where each Rm and Rn is, independently, H, an amino protecting group or substituted or unsubstituted $C_1$-$C_{10}$ alkyl.

In some embodiments, a 2'-substituted nucleoside comprises a sugar moiety comprising a 2'-substituent group selected from F, $OCF_3$, O—$CH_3$, $OCH_2CH_2OCH_3$, $O(CH_2)_2SCH_3$, $O(CH_2)_2$—O—$N(CH_3)_2$, —$O(CH_2)_2O(CH_2)_2N(CH_3)_2$, and O—$CH_2$—C(═O)—$N(H)CH_3$.

In some embodiments, a 2'-substituted nucleoside comprises a sugar moiety comprising a 2'-substituent group selected from F, O—$CH_3$, and $OCH_2CH_2OCH_3$.

In some embodiments, nucleosides of the present disclosure comprise one or more unmodified nucleobases. In certain embodiments, nucleosides of the present disclosure comprise one or more modified nucleobases.

In some embodiments, modified nucleobases are selected from: universal bases, hydrophobic bases, promiscuous bases, size-expanded bases, and fluorinated bases as defined herein. 5-substituted pyrimidines, 6-azapyrimidines and N-2, N-6 and 0-6 substituted purines, including 2-aminopropyladenine, 5-propynyluracil; 5-propynylcytosine; 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl $CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-aminoadenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine ([5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g., 9-(2-aminoethoxy)-H-pyrimido[5,4-13][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deazaadenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, Kroschwitz, J. I., Ed., John Wiley & Sons, 1990, 858-859.

Representative United States patents that teach the preparation of certain of the above noted modified nucleobases as well as other modified nucleobases include without limitation, U.S. Pat. Nos. 3,687,808; 4,845,205; 5,130,302; 5,134, 066; 5,175,273; 5,367,066; 5,432,272; 5,457,187; 5,459, 255; 5,484,908; 5,502,177; 5,525,711; 5,552,540; 5,587, 469; 5,594,121; 5,596,091; 5,614,617; 5,645,985; 5,681, 941; 5,750,692; 5,763,588; 5,830,653 and 6,005,096, each of which is herein incorporated by reference in its entirety.

Additional modifications may also be made at other positions on the oligonucleotide, particularly the 3' position of the sugar on the 3' terminal nucleotide and the 5' position of 5' terminal nucleotide. For example, one additional modification of the ligand conjugated oligonucleotides of the present disclosure involves chemically linking to the oligonucleotide one or more additional non-ligand moieties or conjugates which enhance the activity, cellular distribution or cellular uptake of the oligonucleotide. Such moieties include but are not limited to lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety. In some aspects, a nucleic acid molecule encoding a chimeric hMPV/RSV F protein is a modified RNA, such as, for example, a modified mRNA. Modified (m)RNA contemplates certain chemical modifications that confer increased stability and low immunogenicity to mRNAs, thereby facilitating expression of therapeutically important proteins. For instance, N1-methyl-pseudouridine (N1mΨ) outperforms several other nucleoside modifications and their combinations in terms of translation capacity. In some embodiments, the (m)RNA molecules used herein may have the uracils replaced with psuedouracils such as 1-methyl-3'-pseudouridylyl bases. In some embodiments, some of the uracils are replaced, but in other embodiments, all of the uracils have been replaced. The (m)RNA may comprise a 5' cap, a 5' UTR element, an optionally codon optimized open reading frame, a 3' UTR element, and a poly(A) sequence and/or a polyadenylation signal.

The nucleic acid molecule, whether native or modified, may be delivered as a naked nucleic acid molecule or in a delivery vehicle, such as a lipid nanoparticle. A lipid nanoparticle may comprise one or more nucleic acids present in a weight ratio to the lipid nanoparticles from about 5:1 to about 1:100. In some embodiments, the weight ratio of nucleic acid to lipid nanoparticles is from about 5:1, 2.5:1, 1:1, 1:5, 1:10, 1:15, 1:20, 1:25, 1:30, 1:35, 1:40, 1:45, 1:50, 1:60, 1:70, 1:80, 1:90, or 1:100, or any value derivable therein.

In some embodiments, the lipid nanoparticles used herein may contain one, two, three, four, five, six, seven, eight, nine, or ten lipids. These lipids may include triglycerides, phospholipids, steroids or sterols, a PEGylated lipids, or a group with a ionizable group such as an alkyl amine and one or more hydrophobic groups such as $C_6$ or greater alkyl groups.

In some aspects of the present disclosure, the lipid nanoparticles are mixed with one or more steroid or a steroid derivative. In some embodiments, the steroid or steroid derivative comprises any steroid or steroid derivative. As used herein, in some embodiments, the term "steroid" is a class of compounds with a four ring 17 carbon cyclic structure, which can further comprises one or more substitutions including alkyl groups, alkoxy groups, hydroxy groups, oxo groups, acyl groups, or a double bond between two or more carbon atoms.

In some aspects of the present disclosure, the lipid nanoparticles are mixed with one or more PEGylated lipids (or PEG lipid). In some embodiments, the present disclosure comprises using any lipid to which a PEG group has been attached. In some embodiments, the PEG lipid is a diglyceride which also comprises a PEG chain attached to the glycerol group. In other embodiments, the PEG lipid is a compound which contains one or more C6-C24 long chain alkyl or alkenyl group or a C6-C24 fatty acid group attached to a linker group with a PEG chain. Some non-limiting examples of a PEG lipid includes a PEG modified phosphatidylethanolamine and phosphatidic acid, a PEG ceramide conjugated, PEG modified dialkylamines and PEG modified 1,2-diacyloxypropan-3-amines, PEG modified diacylglycerols and dialkylglycerols. In some embodiments, PEG modified diastearoylphosphatidylethanolamine or PEG modified dimyristoyl-sn-glycerol. In some embodiments, the PEG modification is measured by the molecular weight of PEG component of the lipid. In some embodiments, the PEG modification has a molecular weight from about 100 to about 15,000. In some embodiments, the molecular weight is from about 200 to about 500, from about 400 to about 5,000, from about 500 to about 3,000, or from about 1,200 to about 3,000. The molecular weight of the PEG modification is from about 100, 200, 400, 500, 600, 800, 1,000, 1,250, 1,500, 1,750, 2,000, 2,250, 2,500, 2,750, 3,000, 3,500, 4,000, 4,500, 5,000, 6,000, 7,000, 8,000, 9,000, 10,000, 12,500, to about 15,000. Some non-limiting examples of lipids that may be used in the present disclosure are taught by U.S. Pat. No. 5,820,873, WO 2010/141069, or U.S. Pat. No. 8,450,298, which is incorporated herein by reference.

In some aspects of the present disclosure, the lipid nanoparticles are mixed with one or more phospholipids. In some embodiments, any lipid which also comprises a phosphate group. In some embodiments, the phospholipid is a structure which contains one or two long chain $C_6$-$C_{24}$ alkyl or alkenyl groups, a glycerol or a sphingosine, one or two phosphate groups, and, optionally, a small organic molecule. In some embodiments, the small organic molecule is an amino acid, a sugar, or an amino substituted alkoxy group, such as choline or ethanolamine. In some embodiments, the phospholipid is a phosphatidylcholine. In some embodiments, the phospholipid is distearoylphosphatidylcholine or dioleoylphosphatidylethanolamine. In some embodiments, other zwitterionic lipids are used, where zwitterionic lipid defines lipid and lipid-like molecules with both a positive charge and a negative charge.

In some aspects of the present disclosure, lipid nanoparticle containing compounds containing lipophilic and cationic components, wherein the cationic component is ionizable, are provided. In some embodiments, the cationic ionizable lipids contain one or more groups which is protonated at physiological pH but may deprotonated and has no charge at a pH above 8, 9, 10, 11, or 12. The ionizable cationic group may contain one or more protonatable amines which are able to form a cationic group at physiological pH. The cationic ionizable lipid compound may also further comprise one or more lipid components such as two or more fatty acids with $C_6$-$C_{24}$ alkyl or alkenyl carbon groups. These lipid groups may be attached through an ester linkage or may be further added through a Michael addition to a sulfur atom. In some embodiments, these compounds may be a dendrimer, a dendron, a polymer, or a combination thereof.

In some aspects of the present disclosure, composition containing compounds containing lipophilic and cationic components, wherein the cationic component is ionizable, are provided. In some embodiments, ionizable cationic lipids refer to lipid and lipid-like molecules with nitrogen atoms that can acquire charge (pKa). These lipids may be known in the literature as cationic lipids. These molecules with amino groups typically have between 2 and 6 hydrophobic chains, often alkyl or alkenyl such as $C_6$-$C_{24}$ alkyl or alkenyl groups, but may have at least 1 or more that 6 tails.

In some embodiments, the amount of the lipid nanoparticle with the nucleic acid molecule encapsulated in the pharmaceutical composition is from about 0.1% w/w to about 50% w/w, from about 0.25% w/w to about 25% w/w, from about 0.5% w/w to about 20% w/w, from about 1% w/w to about 15% w/w, from about 2% w/w to about 10% w/w, from about 2% w/w to about 5% w/w, or from about 6% w/w to about 10% w/w. In some embodiments, the amount of the lipid nanoparticle with the nucleic acid molecule encapsulated in the pharmaceutical composition is from about 0.1% w/w, 0.25% w/w, 0.5% w/w, 1% w/w, 2.5% w/w, 5% w/w, 7.5% w/w, 10% w/w, 15% w/w, 20% w/w, 25% w/w, 30% w/w, 35% w/w, 40% w/w, 45% w/w, 50% w/w, 55% w/w, 60% w/w, 65% w/w, 70% w/w, 75% w/w, 80% w/w, 85% w/w, 90% w/w, to about 95% w/w, or any range derivable therein.

In some aspects, the present disclosure comprises one or more sugars formulated into pharmaceutical compositions. In some embodiments, the sugars used herein are saccharides. These saccharides may be used to act as a lyoprotectant that protects the pharmaceutical composition from destabilization during the drying process. These water-soluble excipients include carbohydrates or saccharides such as disaccharides such as sucrose, trehalose, or lactose, a trisaccharide such as fructose, glucose, galactose comprising raffinose, polysaccharides such as starches or cellulose, or a sugar alcohol such as xylitol, sorbitol, or mannitol. In some embodiments, these excipients are solid at room temperature. Some non-limiting examples of sugar alcohols include erythritol, threitol, arabitol, xylitol, ribitol, mannitol, sorbitol, galactitol, fucitol, iditol, inositol, volemitol, isomalt, maltitol, lactitol, maltotritol, maltotetraitol, or a polyglycitol.

In some embodiments, the amount of the sugar in the pharmaceutical composition is from about 25% w/w to about 98% w/w, 40% w/w to about 95% w/w, 50% w/w to about 90% w/w, 50% w/w to about 70% w/w, or from about 80% w/w to about 90% w/w. In some embodiments, the amount of the sugar in the pharmaceutical composition is from about 10% w/w, 15% w/w, 20% w/w, 25% w/w, 30% w/w, 35% w/w, 40% w/w, 45% w/w, 50% w/w, 52.5% w/w, 55% w/w, 57.5% w/w, 60% w/w, 62.5% w/w, 65% w/w, 67.5% w/w, 70% w/w, 75% w/w, 80% w/w, 82.5% w/w, 85% w/w, 87.5% w/w, 90% w/w, to about 95% w/w, or any range derivable therein.

In some embodiments, the pharmaceutically acceptable polymer is a copolymer. The pharmaceutically acceptable polymer may further comprise one, two, three, four, five, or six subunits of discrete different types of polymer subunits. These polymer subunits may include polyoxypropylene, polyoxyethylene, or a similar subunit. In particular, the pharmaceutically acceptable polymer may comprise at least one hydrophobic subunit and at least one hydrophilic subunit. In particular, the copolymer may have hydrophilic subunits on each side of a hydrophobic unit. The copolymer may have a hydrophilic subunit that is polyoxyethylene and a hydrophobic subunit that is polyoxypropylene.

In some embodiments, expression cassettes are employed to express an engineered hMPV F protein, either for subsequent purification and delivery to a cell/subject, or for use directly in a viral-based delivery approach. Provided herein are expression vectors which contain one or more nucleic acids encoding an engineered hMPV F protein.

Expression requires that appropriate signals be provided in the vectors and include various regulatory elements such as enhancers/promoters from both viral and mammalian sources that drive expression of an engineered hMPV F protein in cells. Throughout this application, the term "expression cassette" is meant to include any type of genetic construct containing a nucleic acid coding for a gene product in which part or all of the nucleic acid encoding sequence is capable of being transcribed and translated, i.e., is under the control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene. An "expression vector" is meant to include expression cassettes comprised in a genetic construct that is capable of replication, and thus including one or more of origins of replication, transcription termination signals, poly-A regions, selectable markers, and multipurpose cloning sites.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

In certain embodiments, viral promotes such as the human cytomegalovirus (CMV) immediate early gene promoter, the SV40 early promoter, the Rous sarcoma virus long terminal repeat, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose. By employing a promoter with well-known properties, the level and pattern of expression of the protein of interest following transfection or transformation can be optimized. Further, selection of a promoter that is regulated in response to specific physiologic signals can permit inducible expression of the gene product.

Enhancers are genetic elements that increase transcription from a promoter located at a distant position on the same molecule of DNA. Enhancers are organized much like promoters. That is, they are composed of many individual elements, each of which binds to one or more transcriptional proteins. The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of promoters/enhancers and inducible promoters/enhancers that could be used in combination with the nucleic acid encoding a gene of interest in an expression construct. Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

The promoter and/or enhancer may be, for example, immunoglobulin light chain, immunoglobulin heavy chain, T-cell receptor, HLA DQ a and/or DQ β, β-interferon, interleukin-2, interleukin-2 receptor, MHC class II 5, MHC class II HLA-Dra, β-Actin, muscle creatine kinase (MCK), prealbumin (transthyretin), elastase I, metallothionein (MTII), collagenase, albumin, α-fetoprotein, t-globin, β-globin, c-fos, c-HA-ras, insulin, neural cell adhesion molecule (NCAM), α1-antitrypain, H2B (TH2B) histone, mouse and/or type I collagen, glucose-regulated proteins (GRP94 and GRP78), rat growth hormone, human serum amyloid A (SAA), troponin I (TN I), platelet-derived growth factor (PDGF), SV40, polyoma, retroviruses, papilloma virus, hepatitis B virus, human immunodeficiency virus, cytomegalovirus (CMV), and gibbon ape leukemia virus.

Where a cDNA insert is employed, one will typically desire to include a polyadenylation signal to effect proper polyadenylation of the gene transcript. Any polyadenylation sequence may be employed such as human growth hormone and SV40 polyadenylation signals. Also contemplated as an element of the expression cassette is a terminator. These elements can serve to enhance message levels and to minimize read through from the cassette into other sequences.

There are a number of ways in which expression vectors may be introduced into cells. In certain embodiments, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells. These have a relatively low capacity for foreign DNA sequences and have a restricted host spectrum. Furthermore, their oncogenic potential and cytopathic effects in permissive cells raise safety concerns. They can accommodate only up to 8 kB of foreign genetic material but can be readily introduced in a variety of cell lines and laboratory animals.

One method for in vivo delivery involves the use of an adenovirus expression vector. "Adenovirus expression vector" is meant to include those constructs containing adenovirus sequences sufficient to (a) support packaging of the construct and (b) to express an engineered hMPV F protein that has been cloned therein. In this context, expression does not require that the gene product be synthesized.

The expression vector comprises a genetically engineered form of adenovirus. Knowledge of the genetic organization of adenovirus, a 36 kB, linear, double-stranded DNA virus, allows substitution of large pieces of adenoviral DNA with foreign sequences up to 7 kB. In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target cell range and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off. The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNAs issued from this promoter possess a 5'-tripartite leader (TPL) sequence which makes them preferred mRNAs for translation. In one system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins. Since the E3 region is dispensable from the adenovirus genome, the current adenovirus vectors, with the help of 293 cells, carry foreign DNA in either the E1, the D3 or both regions. In nature, adenovirus can package approximately 105% of the wild-type genome, providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone and is the source of vector-borne cytotoxicity. Also, the replication deficiency of the E1-deleted virus is incomplete.

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

The adenoviruses of the disclosure are replication defective, or at least conditionally replication defective. The adenovirus may be of any of the 42 different known serotypes or subgroups A-F. Adenovirus type 5 of subgroup C is one exemplary starting material that may be used to obtain the conditional replication-defective adenovirus vector for use in the present disclosure.

Other viral vectors may be employed as expression constructs in the present disclosure. Vectors derived from viruses such as vaccinia virus, adeno-associated virus (AAV) and herpesviruses may be employed. They offer several attractive features for various mammalian cells.

In embodiments, particular embodiments, the vector is an AAV vector. AAV is a small virus that infects humans and some other primate species. AAV is not currently known to cause disease. The virus causes a very mild immune response, lending further support to its apparent lack of pathogenicity. In many cases, AAV vectors integrate into the host cell genome, which can be important for certain applications, but can also have unwanted consequences. Gene therapy vectors using AAV can infect both dividing and quiescent cells and persist in an extrachromosomal state without integrating into the genome of the host cell, although in the native virus some integration of virally carried genes into the host genome does occur. These features make AAV a very attractive candidate for creating viral vectors for gene therapy, and for the creation of isogenic human disease models. Recent human clinical trials using AAV for gene therapy in the retina have shown promise. AAV belongs to the genus *Dependoparvovirus*, which in turn belongs to the family Parvoviridae. The virus is a small (20 nm) replication-defective, nonenveloped virus.

Wild-type AAV has attracted considerable interest from gene therapy researchers due to a number of features. Chief amongst these is the virus's apparent lack of pathogenicity. It can also infect non-dividing cells and has the ability to stably integrate into the host cell genome at a specific site (designated AAVS1) in the human chromosome 19. This feature makes it somewhat more predictable than retroviruses, which present the threat of a random insertion and of mutagenesis, which is sometimes followed by development of a cancer. The AAV genome integrates most frequently into the site mentioned, while random incorporations into the genome take place with a negligible frequency. Development of AAVs as gene therapy vectors, however, has eliminated this integrative capacity by removal of the rep and cap from the DNA of the vector. The desired gene together with a promoter to drive transcription of the gene is inserted between the inverted terminal repeats (ITR) that aid in concatemer formation in the nucleus after the single-stranded vector DNA is converted by host cell DNA polymerase complexes into double-stranded DNA. AAV-based gene therapy vectors form episomal concatemers in the host cell nucleus. In non-dividing cells, these concatemers remain intact for the life of the host cell. In dividing cells, AAV DNA is lost through cell division, since the episomal DNA is not replicated along with the host cell DNA. Random integration of AAV DNA into the host genome is detectable but occurs at very low frequency. AAVs also present very low immunogenicity, seemingly restricted to generation of neutralizing antibodies, while they induce no clearly defined cytotoxic response. This feature, along with the ability to infect quiescent cells present their dominance over adenoviruses as vectors for human gene therapy.

The AAV genome is built of single-stranded deoxyribonucleic acid (ssDNA), either positive- or negative-sensed, which is about 4.7 kilobase long. The genome comprises inverted terminal repeats (ITRs) at both ends of the DNA strand, and two open reading frames (ORFs): rep and cap. The former is composed of four overlapping genes encoding Rep proteins required for the AAV life cycle, and the latter contains overlapping nucleotide sequences of capsid proteins: VP1, VP2 and VP3, which interact together to form a capsid of an icosahedral symmetry.

The Inverted Terminal Repeat (ITR) sequences comprise 145 bases each. They were named so because of their symmetry, which was shown to be required for efficient multiplication of the AAV genome. The feature of these sequences that gives them this property is their ability to form a hairpin, which contributes to so-called self-priming that allows primase-independent synthesis of the second DNA strand. The ITRs were also shown to be required for both integration of the AAV DNA into the host cell genome (19th chromosome in humans) and rescue from it, as well as for efficient encapsidation of the AAV DNA combined with generation of a fully assembled, deoxyribonuclease-resistant AAV particles.

With regard to gene therapy, ITRs seem to be the only sequences required in cis next to the therapeutic gene: structural (cap) and packaging (rep) proteins can be delivered in trans. With this assumption many methods were established for efficient production of recombinant AAV (rAAV) vectors containing a reporter or therapeutic gene. However, it was also published that the ITRs are not the only elements required in cis for the effective replication and encapsidation. A few research groups have identified a sequence designated cis-acting Rep-dependent element (CARE) inside the coding sequence of the rep gene. CARE was shown to augment the replication and encapsidation when present in cis.

In some aspects, the present disclosure provides pharmaceutical compositions that contain one or more salts. The salts may be an inorganic potassium or sodium salt such as potassium chloride, sodium chloride, potassium phosphate dibasic, potassium phosphate monobasic, sodium phosphate dibasic, or sodium phosphate monobasic. The pharmaceutical composition may comprise one or more phosphate salts such to generate a phosphate buffer solution. The phosphate buffer solution may be comprise each of the phosphates to buffer a solution to a pH from about 6.8, 6.9, 7.0, 7.1, 7.2, 7.3, 7.4, 7.5, 7.6, 7.7, 7.8, 7.9, or 8.0, or any range derivable therein.

In some aspects, the present disclosure comprises one or more excipients formulated into pharmaceutical compositions. An "excipient" refers to pharmaceutically acceptable carriers that are relatively inert substances used to facilitate administration or delivery of an API into a subject or used to facilitate processing of an API into drug formulations that can be used pharmaceutically for delivery to the site of action in a subject. Furthermore, these compounds may be used as diluents in order to obtain a dosage that can be readily measured or administered to a patient. Non-limiting examples of excipients include polymers, stabilizing agents, surfactants, surface modifiers, solubility enhancers, buffers, encapsulating agents, antioxidants, preservatives, nonionic wetting or clarifying agents, viscosity increasing agents, and absorption-enhancing agents.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, excipient, or vehicle with which the therapeutic is administered. Such pharmaceutical carriers can be sterile liquids, such as water and can preferably include an adjuvant. Water is a particular carrier when the pharmaceutical composition is administered by injections, such an intramuscular injection. Saline solutions and aqueous dextrose and glycerol solutions can also be employed as liquid carriers, particularly for injectable solutions. Other suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulations can include standard carriers such as pharmaceutical grades of mannitol, lactose, starch, magnesium stearate, sodium saccharine, cellulose, magnesium carbonate, etc. Examples of suitable pharmaceutical agents are described in "Remington's Pharmaceutical Sciences." Such compositions will contain a prophylactically or therapeutically effective amount of the antibody or fragment thereof, preferably in purified form, together with a suitable amount of carrier so as to provide the form for proper administration to the patient. The formulation should suit the mode of administration, which can be oral, intravenous, intraarterial, intrabuccal, intranasal, nebulized, bronchial inhalation, or delivered by mechanical ventilation.

Engineered proteins of the present disclosure, as described herein, can be formulated for parenteral administration, e.g., formulated for injection via the intradermal, intravenous, intramuscular, subcutaneous, intra-tumoral or even intraperitoneal routes. The antibodies could alternatively be administered by a topical route directly to the mucosa, for example by nasal drops, inhalation, or by nebulizer. Pharmaceutically acceptable salts include the acid salts and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Generally, the ingredients of compositions of the disclosure are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Dosage can be by a single dose schedule or a multiple dose schedule. Multiple doses may be used in a primary immunization schedule and/or in a booster immunization schedule. In a multiple dose schedule the various doses may be given by the same or different routes. Multiple doses will typically be administered at least 1 week apart (e.g., about 2 weeks, about 3 weeks, about 4 weeks, about 6 weeks, about 8 weeks, about 10 weeks, about 12 weeks, about 16 weeks, etc.).

The compositions disclosed herein may be used to treat both children and adults. Thus, a human subject may be less than 1 year old, 1-5 years old, 5-16 years old, 16-55 years old, 55-65 years old, or at least 65 years old.

Preferred routes of administration include, but are not limited to, intramuscular, intraperitoneal, intradermal, subcutaneous, intravenous, intraarterial, and intraoccular injection. Particularly preferred routes of administration include intramuscular, intradermal and subcutaneous injection.

V. Immunodetection Methods

In still further embodiments, the present disclosure concerns immunodetection methods for binding, purifying, removing, quantifying and otherwise generally detecting hMPV F protein-binding antibodies. While such methods can be applied in a traditional sense, another use will be in quality control and monitoring of vaccine stocks, where antibodies can be used to assess the amount or integrity (i.e., long term stability) of antigens. Alternatively, the methods may be used to screen various antibodies for appropriate/desired reactivity profiles.

Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. In particular, a competitive assay for the detection and quantitation of hMPV F protein-binding antibodies also is provided. In general, the immunobinding methods include obtaining a sample suspected of containing hMPV F protein-binding antibodies, and contacting the sample with an antigen in accordance with the present disclosure, as the case may be, under conditions effective to allow the formation of immunocomplexes.

These methods include methods for detecting or purifying hMPV F protein-binding antibodies or hMPV F protein from a sample. The antigen will preferably be linked to a solid support, such as in the form of a column matrix, and the sample suspected of containing the hMPV F protein-binding antibodies will be applied to the immobilized antigen. The unwanted components will be washed from the column, leaving the hMPV F protein-binding antibodies immunocomplexed to the immobilized antigen, which is then collected by removing the antigen from the column.

The immunobinding methods also include methods for detecting and quantifying the amount of hMPV F protein or related components in a sample and the detection and quantification of any immune complexes formed during the binding process. Here, one would obtain a sample suspected of containing hMPV F protein and contact the sample with an antibody that binds hMPV F protein or components thereof, followed by detecting and quantifying the amount of immune complexes formed under the specific conditions. In terms of antigen detection, the biological sample analyzed may be any sample that is suspected of containing hMPV F protein, such as a tissue section or specimen, a homogenized tissue extract, a biological fluid (e.g., a nasal swab), including blood and serum, or a secretion, such as feces or urine.

Contacting the chosen biological sample with the antigen under effective conditions and for a period of time sufficient to allow the formation of immune complexes (primary immune complexes) is generally a matter of simply adding the antigen composition to the sample and incubating the mixture for a period of time long enough for the antigen to form immune complexes with, i.e., to bind to hMPV F protein-binding antibodies. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

An antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two-step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

1. ELISAs

Immunoassays, in their most simple and direct sense, are binding assays.

Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, the antibodies of the disclosure are immobilized onto a selected surface exhibiting protein affinity, such as a well in a polystyrene microtiter plate. Then, a test composition suspected of containing the hMPV F protein is added to the wells. After binding and washing to remove non-specifically bound immune complexes, the bound antigen may be detected. Detection may be achieved by the addition of another anti-hMPV F protein antibody that is linked to a detectable label. This type of ELISA is a simple "sandwich ELISA." Detection may also be achieved by the addition of a second anti-hMPV F protein antibody, followed by the addition of a third antibody that has binding affinity for the second antibody, with the third antibody being linked to a detectable label.

In another exemplary ELISA, the samples suspected of containing the hMPV F protein (e.g., potentially infected cells) are immobilized onto the well surface and then contacted with the anti-hMPV F protein antibodies of the disclosure. After binding and washing to remove non-specifically bound immune complexes, the bound anti-hMPV F protein antibodies are detected. Where the initial anti-hMPV F protein antibodies are linked to a detectable label, the immune complexes may be detected directly. Again, the immune complexes may be detected using a second antibody that has binding affinity for the first anti-hMPV F protein antibody, with the second antibody being linked to a detectable label.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzothiazoline-6-sulfonic acid (ABTS), or $H_2O_2$, in the case of peroxidase as the enzyme label. Quantification is then achieved by measuring the degree of color generated, e.g., using a visible spectra spectrophotometer.

2. Western Blot

The Western blot (alternatively, protein immunoblot) is an analytical technique used to detect specific proteins in a given sample of tissue homogenate or extract. It uses gel electrophoresis to separate native or denatured proteins by the length of the polypeptide (denaturing conditions) or by the 3-D structure of the protein (native/non-denaturing conditions). The proteins are then transferred to a membrane (typically nitrocellulose or PVDF), where they are probed (detected) using antibodies specific to the target protein.

Samples may be taken from whole tissue or from cell culture. In most cases, solid tissues are first broken down mechanically using a blender (for larger sample volumes), using a homogenizer (smaller volumes), or by sonication. Cells may also be broken open by one of the above mechanical methods. Assorted detergents, salts, and buffers may be employed to encourage lysis of cells and to solubilize proteins. Protease and phosphatase inhibitors are often added to prevent the digestion of the sample by its own enzymes. Tissue preparation is often done at cold temperatures to avoid protein denaturing.

The proteins of the sample are separated using gel electrophoresis. Separation of proteins may be by isoelectric point (pI), molecular weight, electric charge, or a combination of these factors. The nature of the separation depends on the treatment of the sample and the nature of the gel. This is a very useful way to determine a protein. It is also possible to use a two-dimensional (2-D) gel which spreads the proteins from a single sample out in two dimensions. Proteins are separated according to isoelectric point (pH at which they have neutral net charge) in the first dimension, and according to their molecular weight in the second dimension.

In order to make the proteins accessible to antibody detection, they are moved from within the gel onto a membrane made of nitrocellulose or polyvinylidene difluoride (PVDF). The membrane is placed on top of the gel, and a stack of filter papers placed on top of that. The entire stack is placed in a buffer solution which moves up the paper by capillary action, bringing the proteins with it. Another method for transferring the proteins is called electroblotting and uses an electric current to pull proteins from the gel into the PVDF or nitrocellulose membrane. The proteins move from within the gel onto the membrane while maintaining the organization they had within the gel. As a result of this blotting process, the proteins are exposed on a thin surface layer for detection (see below). Both varieties of membrane are chosen for their non-specific protein binding properties (i.e., binds all proteins equally well). Protein binding is based upon hydrophobic interactions, as well as charged interactions between the membrane and protein. Nitrocellulose membranes are cheaper than PVDF, but are far more fragile and do not stand up well to repeated probings. The uniformity and overall effectiveness of transfer of protein from the gel to the membrane can be checked by staining the membrane with Coomassie Brilliant Blue or Ponceau S dyes. Once transferred, proteins are detected using labeled primary antibodies, or unlabeled primary antibodies followed by indirect detection using labeled protein A or secondary labeled antibodies binding to the Fc region of the primary antibodies.

3. Immunohistochemistry

The antibodies of the present disclosure may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections from the capsule. Alternatively, whole frozen tissue samples may be used for serial section cuttings.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections. Again, whole tissue samples may be substituted.

4. Immunodetection Kits

In still further embodiments, the present disclosure concerns immunodetection kits for use with the immunodetection methods described above. As antibodies may be used to detect hMPV F protein, antibodies may be included in the kit. The immunodetection kits will thus comprise, in suitable container means, a first antibody that binds to an hMPV F protein, and optionally an immunodetection reagent. Alternatively, the hMPV F protein antigen may be used to detect hMPV F protein-binding antibodies. In this case, the immunodetection kits will thus comprise, in suitable container means, an hMPV F protein antigen.

In certain embodiments, the antibody or antigen may be pre-bound to a solid support, such as a column matrix and/or well of a microtitre plate. The immunodetection reagents of the kit may take any one of a variety of forms, including those detectable labels that are associated with or linked to an antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with the present disclosure.

The kits may further comprise a suitably aliquoted composition of hMPV F protein, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits of the present disclosure will also typically include a means for containing the antibody, antigen, and any other reagent containers in close confinement for commercial sale. Such containers may include injection or blow-molded plastic containers into which the desired vials are retained.

5. Flow Cytometry and FACS

The antibodies of the present disclosure may also be used in flow cytometry or FACS. Flow cytometry is a laser- or impedance-based technology employed in many detection assays, including cell counting, cell sorting, biomarker detection and protein engineering. The technology suspends cells in a stream of fluid and passing them through an electronic detection apparatus, which allows simultaneous multiparametric analysis of the physical and chemical characteristics of up to thousands of particles per second. Flow cytometry is routinely used in the diagnosis of disorders, but has many other applications in basic research, clinical practice and clinical trials.

Fluorescence-activated cell sorting (FACS) is a specialized type of cytometry. It provides a method for sorting a heterogenous mixture of biological cells into two or more containers, one cell at a time, based on the specific light scattering and fluorescent characteristics of each cell. In general, the technology involves a cell suspension entrained in the center of a narrow, rapidly flowing stream of liquid. The flow is arranged so that there is a large separation between cells relative to their diameter. A vibrating mechanism causes the stream of cells to break into individual droplets. Just before the stream breaks into droplets, the flow passes through a fluorescence measuring station where the fluorescence of each cell is measured. An electrical charging ring is placed just at the point where the stream breaks into droplets. A charge is placed on the ring based immediately prior to fluorescence intensity being measured, and the opposite charge is trapped on the droplet as it breaks form the stream. The charged droplets then fall through an electrostatic deflection system that diverts droplets into containers based upon their charge.

In certain embodiments, to be used in flow cytometry or FACS, the antibodies of the present disclosure are labeled with fluorophores and then allowed to bind to the cells of interest, which are analyzed in a flow cytometer or sorted by a FACS machine.

VI. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Materials and Methods

Protein expression and purification. All hMPV F variants were constructed into a plasmid containing His and StrepTag II tags by Gibson assembly and verified by DNA sequencing. Plasmids encoding F variants and furin at 4:1 ratio were used to co-transfect FreeStyle 293F cells (ThermoFisher) by polyethyleneimine (PEI). Three hours after transfection, kifunensine was added to a final concentration of 5 μM and for large-scale transfections pluronic F-68 was added to a final concentration of 0.1% v/v. Six days after transfection, the filter-sterilized supernatant was applied to a StrepTactin column (IBA) for initial purification, and then to a Superose 6 10/300 or Superdex 200 10/300 size exclusion column (SEC) (GE Healthcare) to obtain a monodisperse fraction in SEC buffer (2 mM Tris pH 8.0, 200 mM NaCl, and 0.03% $NaN_3$). For initial variant screening and characterization, singly substituted and combinatorially substituted hMPV F variants were purified from 40 mL cell cultures. Large-scale expressions of DS-CavEs2 were purified using a Superose 6 16/600 column.

Plasmids encoding the heavy chain and light chain of MPE8 were co-transfected at 1:1 ratio into FreeStyle 293F cells by PEI. A stop codon was introduced before the hinge region of the heavy chain to generate an antigen-binding fragment (Fab) of MPE8. To purify MPE8 Fab, the filter-sterilized supernatant was initially applied to a CaptureSelect™ IgG-CH1 Affinity Matrix (ThermoFisher) and then to a Superdex 200 column (GE Healthcare) to obtain a monodisperse fraction in PBS buffer. All protein samples were concentrated to between 5 and 10 mg/ml, then flash frozen in liquid nitrogen and then stored at −80° C.

Differential scanning fluorimetry. Purified hMPV variants at a final concentration of 1 μM were mixed with a final concentration 5× SYPRO Orange Protein Gel Stain (ThermoFisher) in a white, opaque 96-well plate (VWR). The mixtures were then measured by continuous fluorescence scanning (λex=465 nm, λem=580 nm) using a Roche LightCycler 480 II, with a temperature ramp rate of 4.4° C./minute, and a temperature range of 25° C. to 95° C. Data were plotted as the derivative of the melting curve.

MPE8 binding analysis by biolayer interferometry. To examine the epitope integrity of hMPV F under a variety of temperature stresses, DS-CavEs2 aliquots were incubated at 37° C., 50° C., or 70° C. for 30 min in a thermocycler, or left at 4° C. for 2.5 months prior to being tested for MPE8 binding by BLI using an Octet RED96e (FortdBio). Briefly, anti-human Fab-CH1 2nd generation (FAB2G) biosensors (FortdBio) were used to capture equal amounts of MPE8 Fab at a concentration of 30 nM in a buffer composed of 10 mM HEPES pH 7.4, 150 mM NaCl, 0.005% v/v Tween 20 and 1 mg/ml BSA, Then, the MPE8-captured biosensors were dipped into 50 nM of heat-treated DS-CavEs2 to measure the association rate. After a 600 s association step, a 600 s dissociation step was carried out in wells containing only buffer. The binding curves were aligned to the baseline and buffer subtracted.

Negative stain EM. Postfusion hMPV F was heat treated at 70° C. for 10 min, then applied to a CF-400-Cu grid (Electron Microscopy Sciences) that had been plasma cleaned for 45 seconds in a Solarus 950 plasma cleaner (Gatan) with a 4:1 ratio of $O_2/H_2$. The grid was stained using methylamine tungstate (Nanoprobes). Prefusion-stabilized hMPV F was incubated with a two-fold molar excess of MPE8 Fab in 1×PBS at room temperature for 30 min. The hMPV-F:Fab complexes were diluted to a concentration of 0.03 mg/mL in 2 mM Tris pH 8.0, 200 mM NaCl and 0.02% $NaN_3$, then deposited on a CF-400-Cu grid. Grids were imaged at a magnification of 92,000× (corresponding to a calibrated pixel size of 1.63 Å/pix) in a Talos F200C TEM microscope equipped with a Ceta 16M detector (Thermo Fisher Scientific). CTF-estimation and particle picking were performed in cisTEM (Grant et al., 2018). Particles were then exported to cryoSPARC v2.15.0 for 2D classification (Punjani et al., 2017).

X-ray crystallography for prefusion-stabilized F and complexed with MPE8. DS-CavEs2 crystals were produced by hanging-drop vapor diffusion by mixing 500 nl of DS-CavEs2 (10 mg/ml) with 500 nl of reservoir solution containing 0.1 M MES pH 6.0 and 12% (v/v) PEK 20k. Crystals were soaked in reservoir supplemented with 20% glycerol and frozen in liquid nitrogen. Diffraction data were collected to 2.5 Å at SBC beamline 191D (Advanced Photon Source, Argonne National Laboratory). Crystals of DSx2 in complex with MPE8 Fab were grown by sitting-drop vapor diffusion by mixing 100 nl of the complex (5.4 mg/ml) with 50 nl of reservoir solution containing 10% (v/v) isopropanol, 0.1 M HEPES pH 7.5, and 20% (w/v) PEG4000. Crystals were frozen directly in liquid nitrogen with no added cryoprotectants. Diffraction data for a single crystal that diffracted to 2.2 Å was collected at the SBC beamline 191D (Advanced Photon Source, Argonne National Laboratory). Data were indexed and integrated in iMOSFLM (Battye et al., 2011), before being merged and scaled using Aimless (Evans & Murshudov, 2013). Molecular replacement was performed in Phaser (McCoy et al., 2007), and models were then subjected to multiple rounds of model building and refinement in Coot (Emsley & Cowtan, 2004) and Phenix (Adams et al., 2002), respectively. Data collection and refinement statistics can be found in Table 2.

TABLE 2

Crystallographic data collection and refinement statistics

| | hMPV F DSx2 + MPE8 | hMPV F DS-CavEs2 |
|---|---|---|
| PDB ID | 7SEM | 7SEJ |
| Data collection | | |
| Space group | P2 | P2$_1$ |
| Cell constants | | |
| a, b, c (Å) | 68.2, 45.6, 176.3 | 58.4, 105.8, 91.0 |
| α, β, γ (°) | 90, 94.2, 90 | 90, 105.3, 90 |
| Wavelength (Å) | 0.9792 | 0.9792 |
| Resolution (Å) | 44.0-2.2 (2.28-2.20) | 45.3-2.5 (2.60-2.51) |
| Total reflections | 104,283 (10,509) | 114,529 (2,472) |
| Unique reflections | 54,114 (5,465) | 35,650 (801) |
| R$_{merge}$ | 0.03785 (0.4449) | 0.078 (0.038) |
| R$_{pim}$ | 0.03785 (0.4449) | 0.073 (0.037) |
| I/σI | 9.5 (1.88) | 8.3 (15.5) |
| CC$_{1/2}$ | 0.999 (0.695) | 0.994 (0.994) |
| Completeness (%) | 97.2 (98.1) | 97.6 (96.7) |
| Redundancy | 1.9 (1.9) | 3.2 (3.1) |
| Refinement | | |
| Resolution (Å) | 44.0-2.2 (2.24-2.20) | 43.9-2.5 (2.60-2.51) |
| Unique reflections | 54,074 | 35,578 |
| R$_{work}$/R$_{free}$ (%) | 21.3/24.2 | 22.0/24.9 |
| No. atoms | | |
| Protein | 6,396 | 6,579 |
| Ligand/ion | 42 | 42 |
| Water | 201 | 158 |
| B-factors | | |
| Protein | 60.328 | 43.09 |
| Ligand/ion | 79.46 | 53.27 |
| Water | 51.10 | 43.05 |
| R.m.s. deviations | | |
| Bond lengths (Å) | 0.007 | 0.007 |
| Bond angles (°) | 0.97 | 1.02 |
| Ramachandran | | |
| Favored (%) | 95.7 | 96.3 |
| Allowed (%) | 4.3 | 3.7 |
| Outliers (%) | 0.0 | 0.0 |

Values in parentheses are for the highest-resolution shell.

Enzyme-linked immunosorbent assay. A panel of hMPV F prefusion-specific monoclonal antibodies (MFP10, Ac967, Ac1025 and MPE8) (Corti et al., 2013) or antibodies that are not prefusion-specific (MF11, MF14) (Battles et al., 2017) were individually immobilized on a 96-well microtiter plates overnight at 4° C. Following the blocking step with 1% BSA in PBS, serial dilutions of heat-treated or untreated postfusion hMPV F, starting from 4 ng, were applied to antibody coated wells for 1 h at room temperature. Unbound F was removed by three washes with 0.1% Tween-20 in PBS. The bound F was then detected by adding anti-His-tag mAb conjugated with horseradish peroxidase (HRP) (Bio-Rad), followed by three washes with 0.1% Tween-20 in PBS. HRP substrate (Sigma) was then added for color development and the optical density was read at 492 nm using an ELISA plate reader.

Example 1—Structure-Based Designs of Prefusion-Stabilized hMPV F

Like other class I viral fusion glycoproteins, prefusion hMPV F protein presents as a metastable state and readily transforms into a stable postfusion conformation during triggering. To stabilize F protein in the prefusion state, a proline substitution, A185P, was introduced in a helix-loop-helix region at trimer apex. This substitution allowed for the prefusion structure of hMPV to be obtained, but the low expression level of this construct set back the potential application as a vaccine candidate. Therefore, an H368N substitution, which was shown previously to increase protein expression (Schowalter et al., 2009), similar to the previously described prefusion-stabilized F protein BV-115 (Battles et al., 2017), was also used. From this base construct, 97 variants were designed based on the prefusion (PDB ID: 5WB0) and postfusion (PDB ID: 5L1X) structures of hMPV F, and then each variant was expressed and characterized in terms of production yield, monodispersity, thermostability, and antigenicity. Illustrative variants are shown in Table 3. The strategies employed included disulfide bonds to lock the regions that move substantially during the pre-to-post transitions, hydrophobic residues to fill internal cavities, polar residues to counter internal charge imbalances, and proline substitutions to favor the prefusion conformation and disfavor refolding of F$_1$. The regions that move more than 5 Å during the transition are highlighted in blue in FIG. 1A (Battles et al., 2017), and the best substitutions from each category are indicated in FIG. 1B. Overall, 36 variants with a single substitution increased the protein expression with many variants exhibiting higher thermo stability.

TABLE 3

Illustrative F protein Variants.

| Designation | Mutations (positions relative to any of SEQ ID NOs: 1-7) | Expressed (% rel. to JSM-1147

TABLE 3-continued

Illustrative F protein Variants.

| Designation | Mutations (positions relative to any of SEQ ID NOs: 1-7) | Expressed (% rel. to JSM-1147) | Tm |
|---|---|---|---|
| JM-1 | E26C/G439C | 0 | |
| JM-2 | N46C/L158C | 0 | |
| JM-3 | T49C/A161C | decreased | |
| JM-4 | L50C/V162C | 0 | |
| JM-5 | E51C/R163C | 0 | |
| JM-6 | E51C/K166C | 0 | |
| JM-7 | V104C/N457C | 77 | |
| JM-8 | L110C/N322C | 245 | |
| JM-9 | A113C/D336C | 0 | |
| JM-10 | A113C/D336C, R40M | 0 | |
| JM-11 | A116C/A338C | 40 | |
| JM-12 | A140C/A147C | 310 | |
| JM-13 | S291C/S443C | 60 | |
| JM-14 | S293C/S443C | 0 | |
| JM-15 | S293C/S444C | 0 | |
| JM-16 | S355C/V442C | 0 | |
| JM-17 | G106W | 0 | |
| JM-18 | A107F | 10 | |
| JM-19 | T160M | 0 | |
| JM-20 | L158W | 137 | |
| JM-21 | I128F | 0 | |
| JM-22 | A190M | 0 | |
| JM-23 | S316C/D421C | 0 | |
| JM-24 | T160V | 32 | |
| JM-25 | S149V, I137L | 152 | |
| JM-26 | S149I | 228 | |
| JM-27 | V169I | 51 | |
| JM-28 | N46V | decreased | |
| JM-29 | T49I | | |
| JM-30 | V122L | | |
| JM-31 | S192L | | |
| JM-32 | T317L | | |
| JM-33 | N342P | | |
| JM-34 | E305C/N457C | | |
| JM-36 | S291C/L302C | 0 | |
| JM-37 | V47C/A159C | 0 | |
| JM-38 | T127C/N153C | 275 | +2.2° C. v. JSM-1147 |
| JM-39 | G121C/I258C | 0 | |
| NW-1 | L130P | 120 | |
| NW-2 | L141P | 20 | |
| NW-3 | K142P | 20 | |
| NW-4 | E146P | 250 | |
| NW-5 | L151P | 50 | |
| NW-6 | N153P | 80 | |
| NW-7 | V162P | 80 | |
| NW-8 | D186P | 20 | |
| NW-9 | L187P | 40 | |
| SR-1 | V162F | | |
| SR-2 | V162W | | |
| SR-3 | K188P | | |
| SR-4 | L105I | 65 | |
| SR-5 | L105F | 87 | |
| SR-6 | L105W | 132 | |
| SR-7 | V134I | 87 | |
| SR-8 | H435E | 66 | |
| SR-9 | H435D | 25 | |
| SR-10 | H435N | 45 | |
| SR-11 | K166E | | |
| SR-13 | G53C/K166C | | |
| SR-14 | G53C/V169C | | |
| SR-16 | V231I | 266 | |
| SR-17 | A344P | 200 | |
| SR-18 | S376T | 151 | |
| SR-19 | G366S | 173 | |
| SR-20 | A374V | decreased | |
| SR-21 | S194Q | 108 | |
| SR-22 | I217V | 119 | |
| SR-23 | S355F | 0 | |
| SR-24 | V191I | 80 | |

Example 2—Single-Substitution F Variants

Figure 2B:
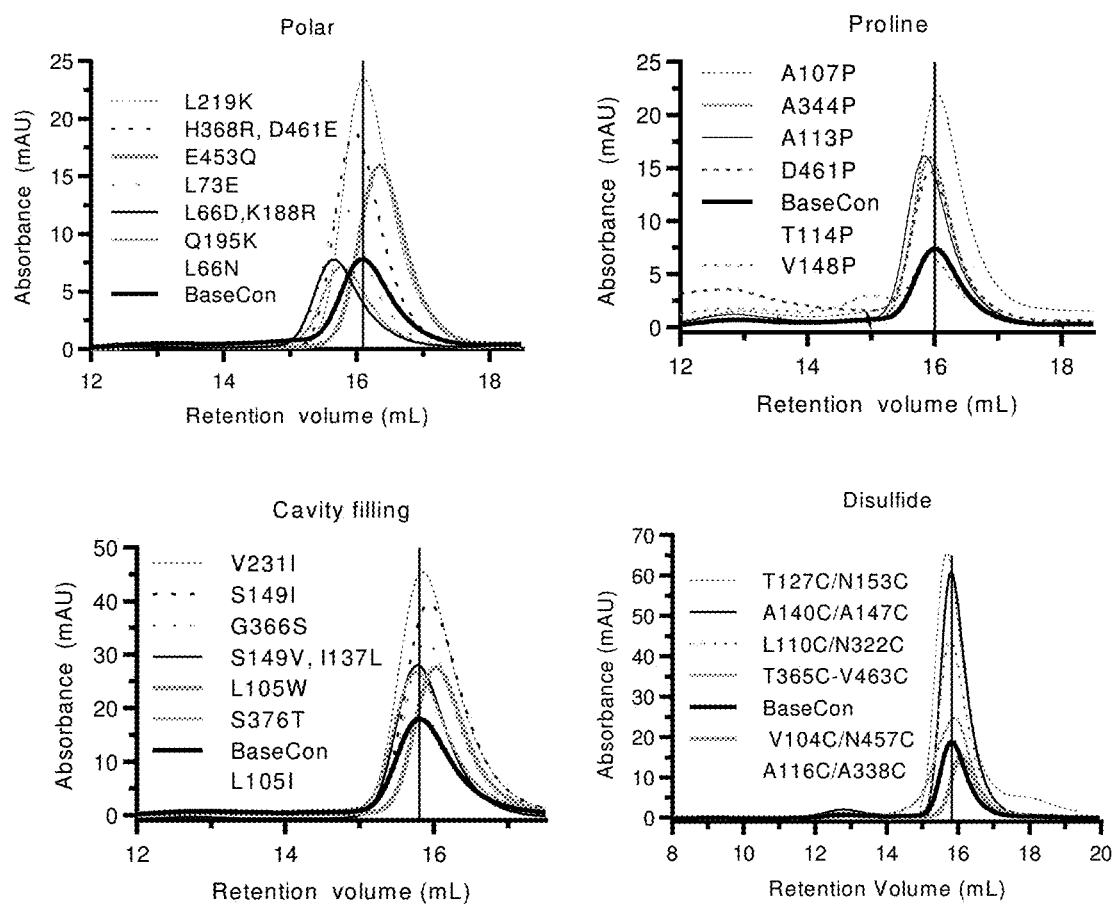
Figure 2C:
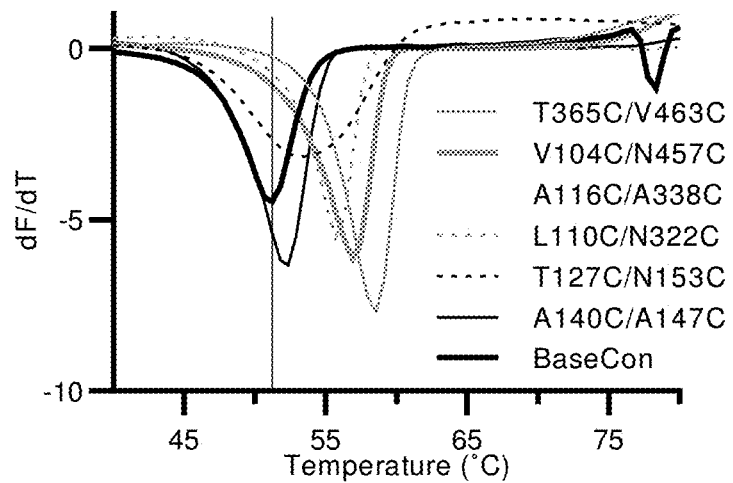
Figure 2D:
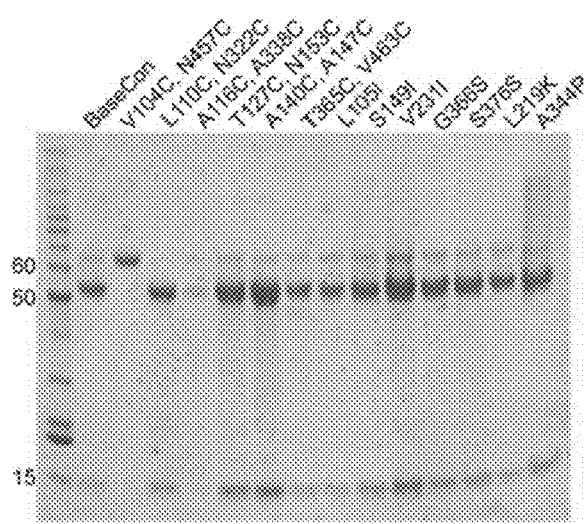
Figure 3A:
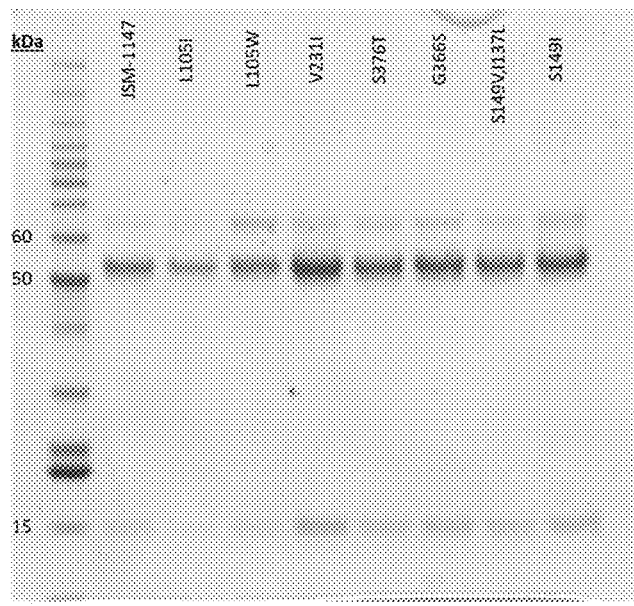
FIGS. 3A-D. Electrophoretic gel images showing expression of various F protein substitution variants.
Figure 3B:
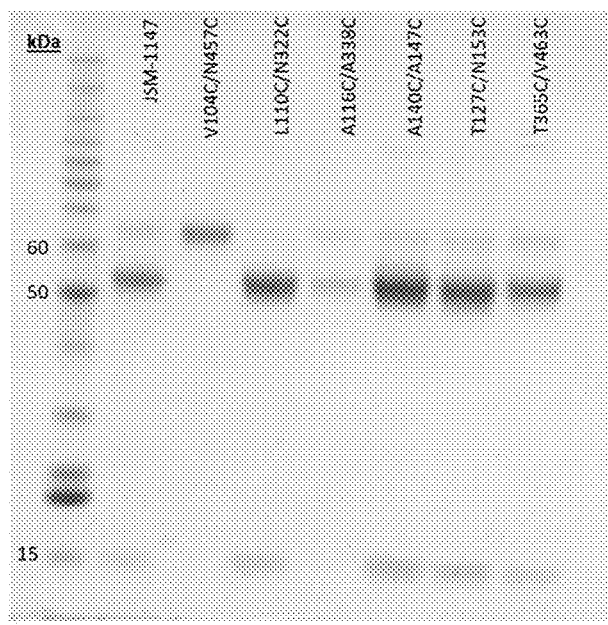
Figure 3C:
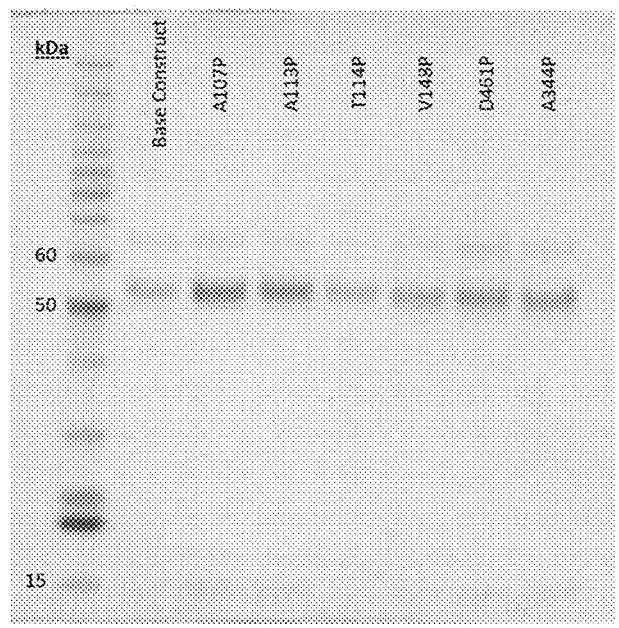
Figure 3D:
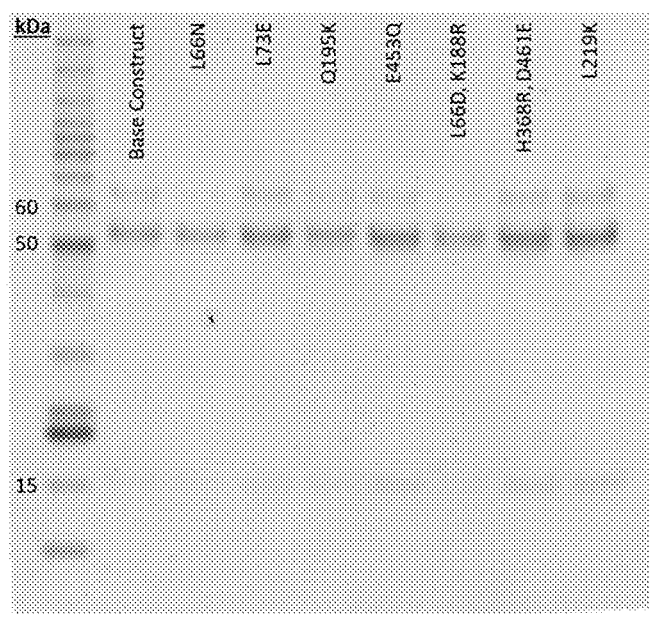
Figure 5:
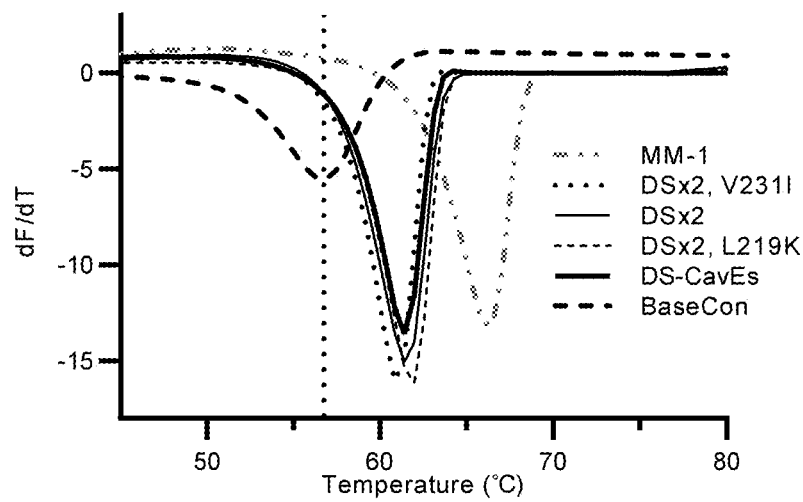
FIG. 5. Differential scanning fluorimetry (DSF) analysis of F protein substitution variant thermostability. The vertical dotted line indicates the first melting temperature for JSM-1147.
Figure 6:
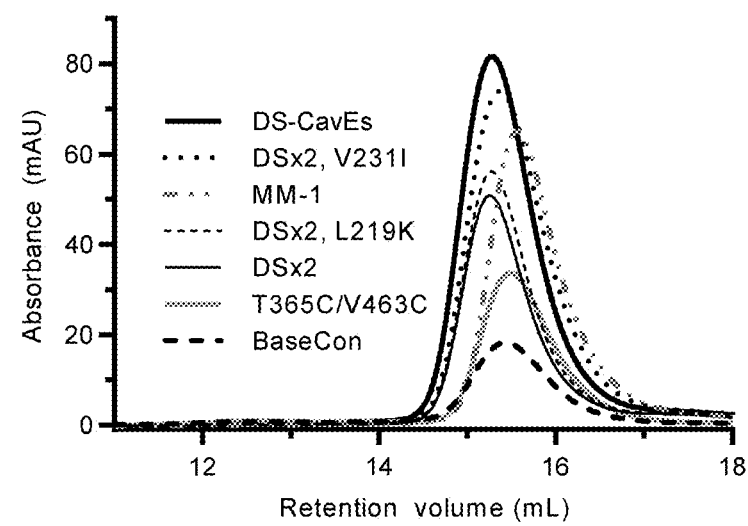
FIG. 6. Size exclusion chromatography of purified F protein substitution variants. The vertical dotted line indicates the characteristic peak retention volume for BaseCon.
Figure 7:
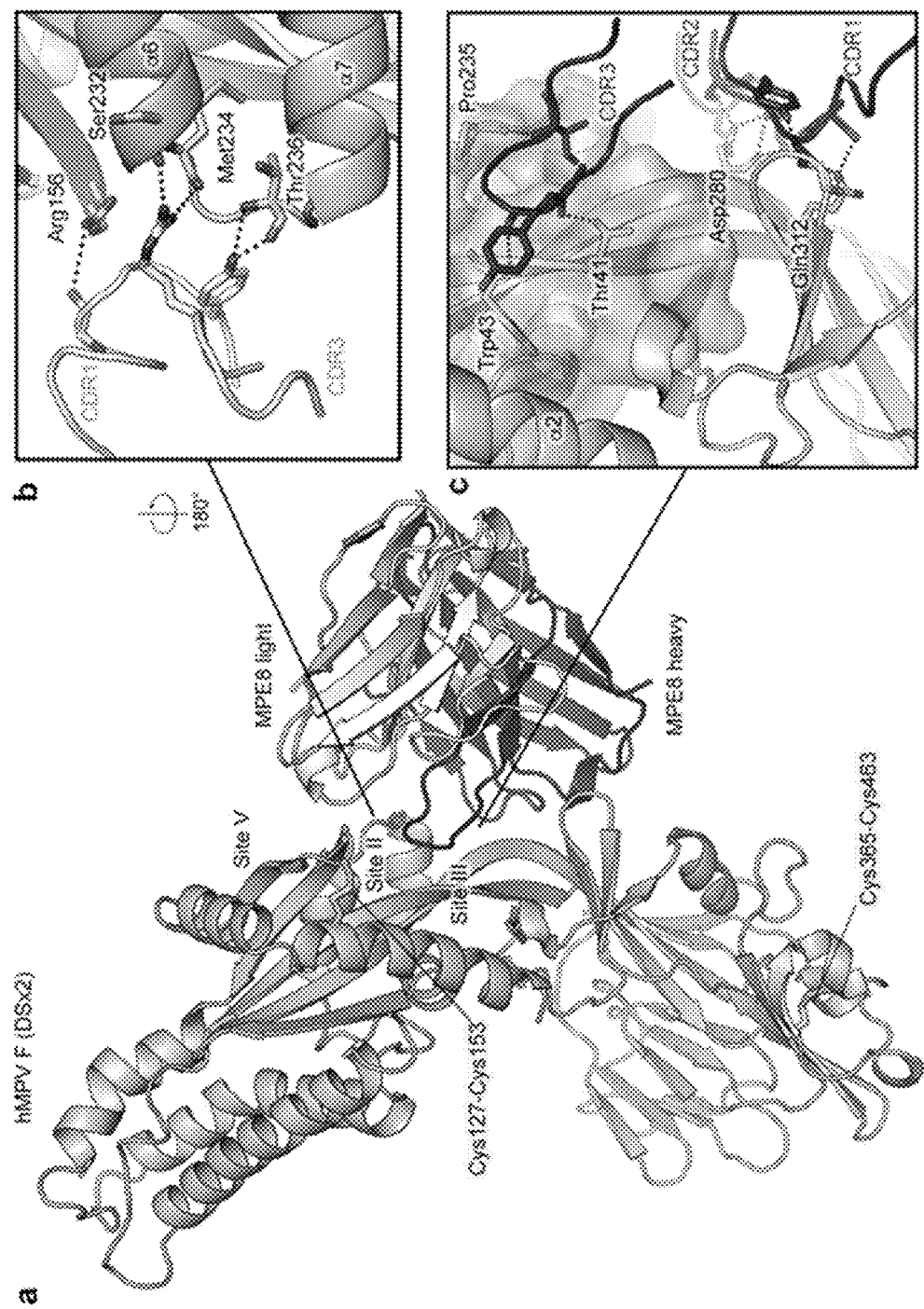
FIGS. 7A-C. Engineered hMPV F variant bound to a prefusion-preferred antibody MPE8.

The expression profiles of 42 individual variants are summarized in FIG. 2A and the size-exclusion chromatography (SEC) traces of select variants from each design category are shown in FIG. 2B. Note that through this Example, values of fold changes in protein yield provided in brackets relate to the original values determined when each of the constructs was designed. The value given in Table 3 are from experiments where all constructs were re-expressed and purified in parallel, and the area under curve on the SEC chromatogram compared to the base construct control for each experiment. In the re-expression, all constructs expressed better than in the original expressions. Low yield of the base construct in the original expression was the main contributor for the higher fold yield values in the original values.

Nine variants with proline substitutions were designed, expressed, and characterized. Six out of nine variants enhanced the protein expression (FIGS. 2A,B). Two variants, A107P and A113P, are both located within the fusion peptide and exhibited 2.9- and 1.9-fold increases [5.1- and 3.3-fold increases] in protein yield, respectively, relative to the base construct (FIG. 2B). Of note, A107P exhibited a rightward shift of the SEC peak relative to the base construct, suggesting a more compact trimer structure (FIG. 2B). A344P, the only substitution at domain I (site I) designed to cap a helix, showed 2-fold increases in protein yield but slightly decreased Tm by ~0.6° C. The design of D461P was also attempted to cap α10 at HRB, which leads to a 1.8-fold increase [2.2-fold increase] in protein yield and a rightward shift of SEC peak relative to the base construct, indicating a more compact trimer structure. Finally, T114P, E146P, and V148P all increased the protein expression.

A salt bridge was engineered into the MPV F protein to neutralize internal charge imbalance. L73E and L219K increased the protein expression by 1.5- and 1.4-fold [2.6- and 1.4-fold], respectively (FIGS. 2A,B), and both showed longer retention times in SEC. A pair of substitutions, L66D/K188R, were introduced that increased the expression by 1.6 fold. E453Q exhibited a 1.9-fold increase [2.8-fold increase] in protein yield but also a significant rightward shift of trimer peak on SEC, suggesting trimer could be in a relatively closed conformation (FIG. 2C). In addition, several cavity filling variants showed beneficial effect on stabilizing F protein. For instance, V231I at domain IIIb (site II) increased the protein expression by 2.7-fold [3.6-fold] (FIGS. 2A,B). One other variant, S376T, also showed a 2.4-fold increase in protein yield relative to the base construct. Two other variants, S149I and G366S, showed 2.3- and 1.7-fold increases [2.3- and 2.9-fold increases] in protein expression relative to the base construct and eluted as monodisperse peaks on SEC.

Prefusion stabilizing disulfide bridges were tested for hMPV F to improve protein expression and thermostability. Two examples, L110C/N322C and T365C/V463C, showed 2.5- and 1.7-fold increases [2.8- and 2.4-fold increases] in protein yield and 5.6° C. and 6.2° C. increases in Tm relative to the base construct, respectively (FIGS. 2,A,B,C). The variant, A116C/A338C, also improved the thermostability but did not increase the expression compared to the base construct. On the other hand, A140C/A147C and T127C/N153C were all located at domain IIIa (site V) (i.e., within α2, α3, β3 and β4 (FIG. 1B)), and significantly increased the protein expression by 3.1 and 2.8 fold [6.0 and 4.8 fold] (FIGS. 2A,B), respectively. T127C/N153C moderately improved the thermostability (FIG. 2C). The V104C/N457C variant showed reduced cleavage by furin (FIG. 2D), had increased Tm by 4° C., and showed decreased protein expression level relative to the base construct (FIGS. 2B,C). Overall, about 20 of the 42 variants increased protein expression (FIG. 2A) with 6 variants exhibiting increased thermostability.

Example 3—Multiple-Substitution F Variants

Combinations of single substitutions were engineered into three different variants containing either two disulfide bonds, one disulfide bond with one cavity filling, or one disulfide bond with one salt bridge were generated. The substitution T365C/V463C was included in all three combinational variants due to its significant improvement in thermostability. All three variants (T127C/N153C/T365C/V463C, V231I/T365C/V463C, L219K/T365C/V463C) exhibited further 1.2-, 1.9-, 1.2-fold increases in protein yield relative to its parental construct T365C/V463C, and the Tm of the variant containing two disulfide bonds further increased 1.7° C. relative to the parental T365C/V463C construct and 6.4° C. relative to the base construct (FIGS. 4A,D). The T127C/N153C/T365C/V463C variant was named DSx2, and either L219K or V231I was further engineered into it. DSx2/L219K and DSx2/V231I showed additional 1.1- and 1.6-fold increases compared to DSx2 (FIG. 4B,6). Furthermore, a variant containing all beneficial mutations (T127C/N153C/T365C/V463C/L219K/V231I) produced 16 mg of protein from 1 L of FreeStyle 293-F cells, exhibiting the highest expression level among all the constructs for an additional 1.8-fold increase compared to DSx2 and had a Tm of 60.7° C. (FIG. 4D,5). This variant was renamed DS-CavEs and one more disulfide bond design (L110C/N322C) was further engineered into DS-CavEs to generate a penta-substituted variant named MM-1 (T127C/N153C/T365C/V463C/L219K/V231I/L110C/N322C). For MM-1, protein expression was decreased by 25% relative to DS-CavEs and showed a substantial improvement in Tm (67.6° C.). Another variant, named MM-1H (T127C/N153C/T365C/V463C/L219K/V231I//L110C/N322C/N386H), was made by reverting H368N back to the wildtype His368 relative to MM-1. For MM-1H, protein expression was decreased by 25% relative to DS-CavEs and showed an increased Tm (65.2° C.) (FIGS. 4C,D). This enhancement of thermostability due to the introduction of L110C/N322C could be very advantageous for vaccine antigens. Due to the benefits shown by additional disulfide bonds, introduction of A140C/A147C was explored based on its favorable expression profile as a single substitution (FIG. 2B). This construct, referred to as MM-4H, exhibited a minimal difference in expression yield and a Tm increase of 1.0° C. (FIGS. 4C,D).

Furthermore, A140C/A147C and E453Q substitutions were introduced to MM-1H, which also corresponds to introducing E453Q to MM-4H and named DS-CavEs2. Large-scale expression of DS-CavEs-2 yields 15.7 mg of prefusion-stabilized F from 1 L of FreeStyle 293-F cells (FIG. 4E). The antigenic surface of DS-CavEs2 is well-preserved. The affinity of DS-CavEs2 to prefusion specific antibody MPE8 (Wen et al., 2017) is comparable to that of base construct, being unaltered after 50° C. incubation for 30 min (FIG. 4F). From nsEM analysis, DS-CavEs2 appears a well-folded prefusion trimer and each protomer was bound by MPE8 Fab. DS-CavEs2 with the additional substitutions enhances the expression by more than 10-fold and exhibits the highest thermostability (Tm 71.8° C.) (FIG. 4D) with correct prefusion conformation, suggesting potential for vaccine development.

Example 4—Crystal Structure of MPE8-Bound DSx2 Construct

For the combinatorial mutation DSx2 construct, the crystal structure of the protein complexed with the prefusion-specific antibody MPE8 was obtained to determine the effect of multiple substitutions on the conformation of hMPV F. The protein complex crystallized in the space group P2 and diffracted X-rays to a resolution of 2.2 Å. After model building and refinement, the structure was originally found to have an $R_{work}$ and $R_{free}$ of 19.68% and 23.5%, respectively, which upon further refinement of the structure improved to 21.3% and 24.2%, respectively (Table 2). In comparison with the previously determined hMPV F structure (PDBID: 5WB0), DSx2 retained the prefusion conformation with an overall RMSD of 1.8 Å for 427 Cα residues (FIG. 9).

Example 5—Structure of MPE8 Bound DS-CavEs2

Figure 8:
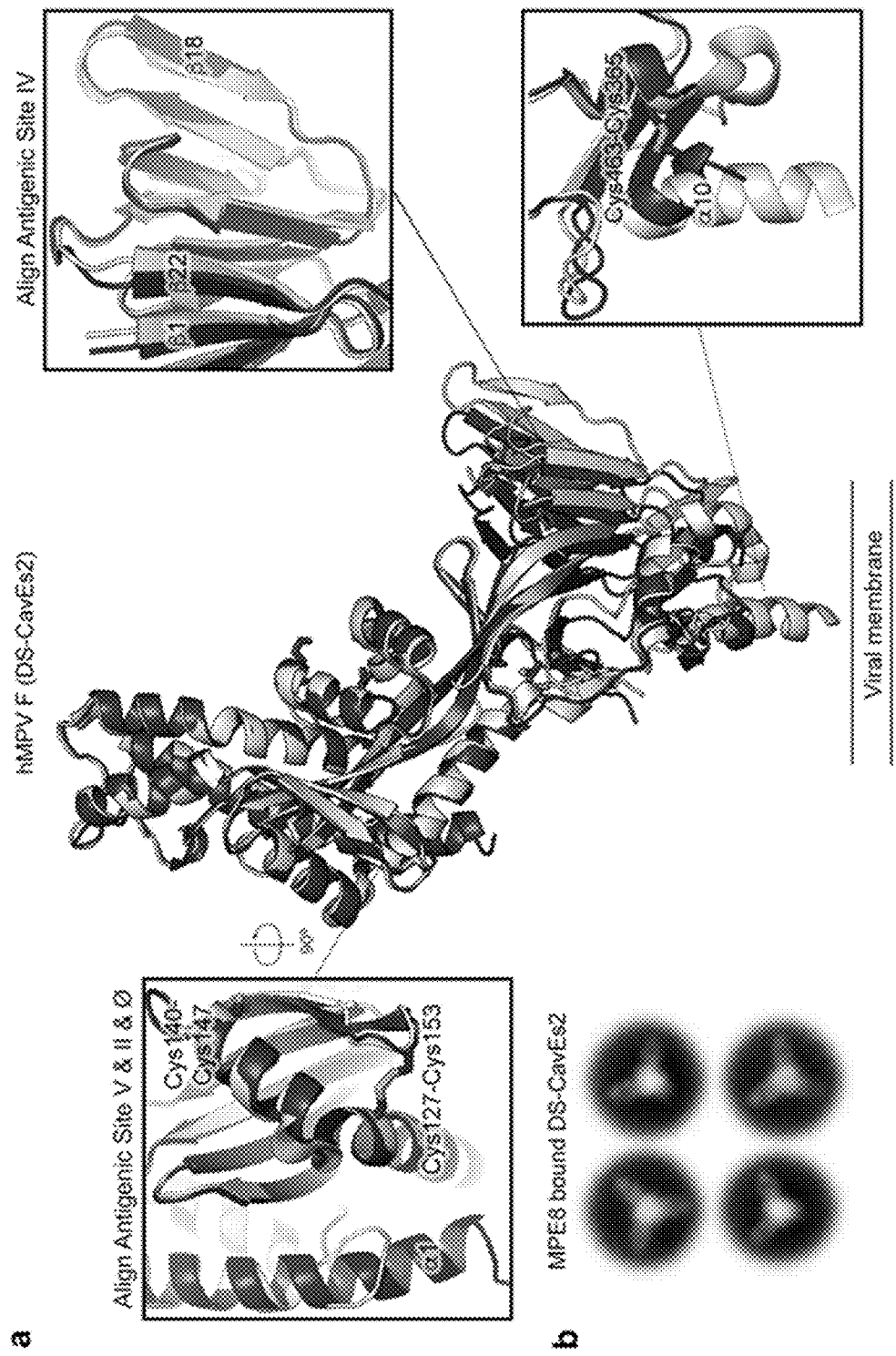
FIGS. 8A-B. The structure of hMPV F DS-CavEs2 exhibits a prefusion conformation.

The crystal structure of DS-CavEs2 was determined to a resolution of 2.5 Å from a crystal in space group $P2_1$ (Table 2). In the absence of MPE8, DS-CavEs2 retained the prefusion conformation, with an RMSD of 2.3 Å over 428 Cα atoms shared with PDBID: 5WB0 (FIG. 8A). Unambiguous electron density was observed for all disulfide bond substitutions (Cys127/Cys153, Cys140/Cys147, Cys110/Cys322, Cys365/Cys463) and the cavity-filling substitution (I231). Superposition of the membrane-distal half (sites II, V and Ø) of DS-CavEs2 with a previous hMPV F structure (PDBID: 5WB0) revealed a substantial movement of antigenic site IV toward the central 3-fold axis (FIG. 8A). Superposition of site IV from both structures demonstrated that there is a rigid-body flexing at the center of the two long β strands (β1 and β22) that connect the upper and lower halves of the F protein (FIG. 8A). Similar to the DSx2 structure, the two disulfide-bond substitutions at site V did not alter the local conformation. In contrast, the Cys365/Cys463 substitution pulled the α10 helix away from the central 3-fold axis and thus altered the downward trajectory of the HRB (FIG. 8A). Negative stain electron microscopy (nsEM) analysis was performed on MPE8 complexed to DS-CavEs2. After 2D class averaging, multiple classes showed DS-CavEs2 as a well-folded prefusion trimer bound by two or three MPE8 Fabs, demonstrating that DS-CavEs2 can adopt a trimeric conformation (FIG. 8B).

Example 6—Prefusion-Stabilized hMPV F Variants as Immunogens

To investigate whether the prefusion-stabilized hMPV F variants function as immunogens, BALB/c mice with will be immunized with either prefusion (e.g., base construct, DSx2 and DS-CavEs2) or postfusion F antigens adjuvanted with CpG three weeks apart. Sera will be collected 10 days after the second immunization. It is expected that prefusion-stabilized F constructs will elicit higher neutralizing antibody titers against hMPV A1 and/or hMPV B1 relative to the postfusion F antigen.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Adams, P. D. et al. PHENIX: building new software for automated crystallographic structure determination. Acta crystallographica. Section D, Biological crystallography 58, 1948-1954 (2002).

Baden, L. R. et al. Efficacy and Safety of the mRNA-1273 SARS-CoV-2 Vaccine. The New England journal of medicine (2020) doi:10.1056/NEJMoa2035389.

Bangaru, S. et al. A Site of Vulnerability on the Influenza Virus Hemagglutinin Head Domain Trimer Interface. Cell 177, 1136-1152.e18 (2019).

Battles, M. B. et al. Structure and immunogenicity of pre-fusion-stabilized human metapneumovirus F glycoprotein. Nature communications 8, 1528 (2017).

Battye, T. G. G., Kontogiannis, L., Johnson, O., Powell, H. R. & Leslie, A. G. W. iMOSFLM: a new graphical interface for diffraction-image processing with MOSFLM. Acta crystallographica. Section D, Biological crystallography 67, 271-281 (2011).

Benjamini, Y., Krieger, A. M. & Yekutieli, D. Adaptive linear step-up procedures that control the false discovery rate. Biometrika 93, 491-507 (2006).

Corti, D. et al. Cross-neutralization of four paramyxoviruses by a human monoclonal antibody. Nature 501, 439-443 (2013).

Crank, M. C. et al. A proof of concept for structure-based vaccine design targeting RSV in humans. Science 365, 505-509 (2019).

Emsley, P. & Cowtan, K. Coot: Model-building tools for molecular graphics. Acta Crystallographica Section D: Biological Crystallography 60, 2126-2132 (2004).

Evans, P. R. & Murshudov, G. N. How good are my data and what is the resolution? Acta crystallographica. Section D, Biological crystallography 69, 1204-1214 (2013).

Gilman, M. S. A. et al. Transient opening of trimeric prefusion RSV F proteins. Nature Communications 10, 2105 (2019).

Gilman, M. S. A. et al. Rapid profiling of RSV antibody repertoires from the memory B cells of naturally infected adult donors. Science Immunology 1, eaaj1879 (2016).

Graham, B. S. Vaccine development for respiratory syncytial virus. Current opinion in virology 23, 107-112 (2017).

Grant, T., Rohou, A. & Grigorieff, N. cisTEM, user-friendly software for single-particle image processing. eLife 7, (2018).

Hamelin, M. È. & Boivin, G. Human metapneumovirus. Seminars in Respiratory and Critical Care Medicine 28, 213-221 (2007).

Hsieh, C.-L. et al. Structure-based design of prefusion-stabilized SARS-CoV-2 spikes. Science 369, 1501 LP-1505 (2020).

Huang, J., Diaz, D. & Mousa, J. J. Antibody recognition of the Pneumovirus fusion protein trimer interface. PLoS pathogens 16, e1008942 (2020).

Jiachen, H. et al. Structure, Immunogenicity, and Conformation-Dependent Receptor Binding of the Postfusion Human Metapneumovirus F Protein. Journal of Virology 95, e00593-21 (2021).

Joyce, M. G. et al. Iterative structure-based improvement of a fusion-glycoprotein vaccine against RSV. Nature structural & molecular biology 23, 811-820 (2016).

Keech, C. et al. Phase 1-2 Trial of a SARS-CoV-2 Recombinant Spike Protein Nanoparticle Vaccine. The New England journal of medicine 383, 2320-2332 (2020).

Krarup, A. et al. A highly stable prefusion RSV F vaccine derived from structural analysis of the fusion mechanism. Nature communications 6, 8143 (2015).

Magro, M. et al. Neutralizing antibodies against the preactive form of respiratory syncytial virus fusion protein offer unique possibilities for clinical intervention. Proceedings of the National Academy of Sciences of the United States of America 109, 3089-3094 (2012).

Más, V. et al. Engineering, Structure and Immunogenicity of the Human Metapneumovirus F Protein in the Postfusion Conformation. PLoS pathogens 12, e1005859 (2016).

McCoy, A. J. et al. Phaser crystallographic software. Journal of applied crystallography 40, 658-674 (2007).

McLellan, J. S. et al. Structure-based design of a fusion glycoprotein vaccine for respiratory syncytial virus. Science (New York, N.Y.) 342, 592-598 (2013).

Punjani, A., Rubinstein, J. L., Fleet, D. J. & Brubaker, M. A. cryoSPARC: algorithms for rapid unsupervised cryo-EM structure determination. Nature methods 14, 290-296 (2017).

Rutten, L. et al. Structure-Based Design of Prefusion-Stabilized Filovirus Glycoprotein Trimers. Cell reports 30, 4540-4550.e3 (2020).

Rutten, L. et al. A Universal Approach to Optimize the Folding and Stability of Prefusion-Closed HIV-1 Envelope Trimers. Cell reports 23, 584-595 (2018).

Sanders, R. W. et al. A next-generation cleaved, soluble HIV-1 Env trimer, BG505 SOSIP.664 gp140, expresses multiple epitopes for broadly neutralizing but not non-neutralizing antibodies. PLoS pathogens 9, e1003618 (2013).

Sastre, P., Melero, J. A., García-Barreno, B. & Palomo, C. Comparison of affinity chromatography and adsorption to vaccinia virus recombinant infected cells for depletion of antibodies directed against respiratory syncytial virus glycoproteins present in a human immunoglobulin preparation. Journal of medical virology 76, 248-255 (2005).

Schickli, J. H., Kaur, J., Ulbrandt, N., Spaete, R. R. & Tang, R. S. An S101P substitution in the putative cleavage motif of the human metapneumovirus fusion protein is a major determinant for trypsin-independent growth in vero cells and does not alter tissue tropism in hamsters. Journal of virology 79, 10678-10689 (2005).

Shafagati, N. & Williams, J. Human metapneumovirus—what we know now [version 1; referees: 2 approved] Referee Status: F1000 Research 7, 1-11 (2018).

Shirogane, Y. et al. Efficient Multiplication of Human Metapneumovirus in Vero Cells Expressing the Transmembrane Serine Protease TMPRSS2. Journal of Virology 82, 8942-8946 (2008).

Skiadopoulos, M. H. et al. Individual contributions of the human metapneumovirus F, G, and SH surface glycoproteins to the induction of neutralizing antibodies and protective immunity. Virology 345, 492-501 (2006).

Stewart-Jones, G. B. E. et al. Structure-based design of a quadrivalent fusion glycoprotein vaccine for human parainfluenza virus types 1-4. Proceedings of the National Academy of Sciences of the United States of America 115, 12265-12270 (2018).

van den Hoogen, B. G. et al. A newly discovered human pneumovirus isolated from young children with respiratory tract disease. Nature medicine 7, 719-724 (2001).

van den Hoogen, B. G., Bestebroer, T. M., Osterhaus, A. D. M. E. & Fouchier, R. A. M. Analysis of the genomic sequence of a human metapneumovirus. Virology 295, 119-132 (2002).

Watanabe, A. et al. Antibodies to a Conserved Influenza Head Interface Epitope Protect by an IgG Subtype-Dependent Mechanism. Cell 177, 1124-1135.e16 (2019).

Wen, X. et al. Structure of the human metapneumovirus fusion protein with neutralizing antibody identifies a pneumovirus antigenic site. Nature structural & molecular biology 19, 461-463 (2012).

Wen, X. et al. Structural basis for antibody cross-neutralization of respiratory syncytial virus and human metapneumovirus. Nature microbiology 2, 16272 (2017).

Williams, K. et al. Phase 1 Safety and Immunogenicity Study of a Respiratory Syncytial Virus Vaccine With an Adenovirus 26 Vector Encoding Prefusion F (Ad26.RSV.preF) in Adults Aged ≥60 Years. The Journal of infectious diseases 222, 979-988 (2020).

Wrapp, D. et al. Cryo-EM structure of the 2019-nCoV spike in the prefusion conformation. Science 367, 1260 LP-1263 (2020).

What is claimed is:

1. A nucleic acid molecule comprising a nucleotide sequence that encodes an amino acid sequence of an engineered protein comprising a metapneumovirus (MPV) F protein ectodomain having at least 90% identity to amino acids 19-489 of any one of SEQ ID NOs: 4-7, said engineered protein comprising an engineered disulfide bond comprising paired cysteine substitutions corresponding to T127C and N153C and/or L110C and N322C, relative to the sequence of any one of SEQ ID NOs: 4-7, wherein the nucleic acid molecule is an mRNA molecule.

2. The nucleic acid molecule of claim 1, wherein the engineered protein further comprises substitutions at positions corresponding to L219 and/or V231.

3. The nucleic acid molecule of claim 1, wherein the engineered protein further comprises substitutions corresponding to L219K and V231I.

4. The nucleic acid molecule of claim 1, wherein the engineered protein further comprises paired cysteine substitutions corresponding to T365C and V463C.

5. The nucleic acid molecule of claim 1, wherein the engineered protein comprises paired cysteine substitutions corresponding to T127C and N153C and to T365C and V463C and a substitution corresponding to L219K.

6. The nucleic acid molecule of claim 1, wherein the engineered protein comprises paired cysteine substitutions corresponding to T127C and N153C and to T365C and V463C and a substitution corresponding to V231I.

7. The nucleic acid molecule of claim 1, wherein the engineered protein further comprises a proline substitution corresponding to A/D185P.

8. The nucleic acid molecule of claim 1, wherein the engineered protein further comprises a substitution of residues corresponding to positions 87-104 of any one of SEQ ID NOs: 4-7 to GGGGSGGGGSR (SEQ ID NO: 8).

9. The nucleic acid molecule of claim 1, wherein the engineered protein further comprises an electrostatic interaction substitution at a position corresponding to L66, L73, N145, Q195, E453, K188, H368, D461, T49 and/or V262.

10. The nucleic acid molecule of claim 9, wherein the electrostatic interaction substitution comprises a substitution corresponding to L66N, L73E, N145E, Q195K, E453Q, L66D, K188R, H368R, D461E, T49E, and/or V262D.

11. The nucleic acid molecule of claim 1, wherein the engineered protein comprises substitutions corresponding to T127C, N153C, T365C, V463C, L219K, and V231I.

12. The nucleic acid molecule of claim 1, wherein the engineered protein comprises substitutions corresponding to T127C, N153C, A185P, T365C, V463C, L219K, and V231I.

13. The nucleic acid molecule of claim 1, wherein the engineered protein comprises substitutions corresponding to T127C, N153C, A185P, T365C, V463C, L219K, V231I, and RQSR (residues corresponding to positions 99-102 of any one of SEQ ID NOs: 4-7) to RRRR (SEQ ID NO: 10).

14. The nucleic acid molecule of claim 1, wherein the engineered protein comprises substitutions corresponding to L110C, T127C, A140C, A147C, N153C, L219K, V231I, N322C, T365C, E453Q, and V463C.

15. The nucleic acid molecule of claim 1, wherein the engineered protein comprises substitutions corresponding to L110C, T127C, A140C, A147C, N153C, A185P, L219K, V231I, N322C, T365C, E453Q, and V463C.

16. The nucleic acid molecule of claim 1, wherein the engineered protein comprises substitutions corresponding to L110C, T127C, A140C, A147C, N153C, A185P, L219K, V231I, N322C, T365C, E453Q, V463C, and RQSR (residues corresponding to positions 99-102 of any one of SEQ ID NOs: 4-7) to RRRR (SEQ ID NO: 10).

17. The nucleic acid molecule of claim 1, wherein the engineered protein comprises a polypeptide sequence at least 95% identical to SEQ ID NO: 14.

18. The nucleic acid molecule of claim 1, wherein the engineered protein comprises a polypeptide sequence at least 95% identical to SEQ ID NO: 15.

19. The nucleic acid molecule of claim 1, wherein the engineered protein comprises a polypeptide sequence having at least 95% identity to the amino acid sequence of SEQ ID NO: 2.

20. The nucleic acid molecule of claim 1, wherein the engineered protein comprises an hMPV F protein ectodomain having at least 95% identity to amino acids 19-489 of SEQ ID NO: 4.

21. The nucleic acid molecule of claim 1, wherein the engineered protein is fused to a trimerization domain.

22. The nucleic acid molecule of claim 21, wherein the trimerization domain comprises a T4 fibritin trimerization domain.

23. The nucleic acid molecule of claim 1, wherein the engineered protein is fused to a transmembrane domain.

24. The nucleic acid molecule of claim 1, wherein the engineered protein comprises an N-terminal signal sequence.

25. A pharmaceutical composition comprising a pharmaceutically acceptable carrier and the nucleic acid molecule of claim 1.

26. The pharmaceutical composition of claim 25, further comprising an adjuvant.

27. A method of preventing metapneumovirus (MPV) infection or a disease associated with metapneumovirus infection in a subject, comprising administering to the subject an effective amount of the nucleic acid molecule of claim 1.

28. A nucleic acid molecule comprising a nucleotide sequence that encodes an amino acid sequence of an engineered protein comprising a metapneumovirus (MPV) F protein ectodomain having the amino acid sequence of SEQ ID NO: 15, wherein the nucleic acid molecule is an mRNA molecule.

* * * * *